(12) United States Patent
Grunstein

(10) Patent No.: US 8,461,125 B2
(45) Date of Patent: Jun. 11, 2013

(54) COMPOSITIONS AND METHODS TO TREAT ASTHMA

(75) Inventor: Michael M. Grunstein, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 12/856,130

(22) Filed: Aug. 13, 2010

(65) Prior Publication Data

US 2011/0014133 A1 Jan. 20, 2011

Related U.S. Application Data

(63) Continuation-in-part of application No. PCT/US2009/034300, filed on Feb. 17, 2009.

(60) Provisional application No. 61/028,699, filed on Feb. 14, 2008.

(51) Int. Cl.
*C12N 15/11* (2006.01)
*C07H 21/02* (2006.01)

(52) U.S. Cl.
USPC ........................................ 514/44 A; 536/24.5

(58) Field of Classification Search
None
See application file for complete search history.

(56) References Cited

U.S. PATENT DOCUMENTS

| 6,410,714 | B1 | 6/2002 | Weber et al. | |
|---|---|---|---|---|
| 7,056,704 | B2 * | 6/2006 | Tuschl et al. | 435/91.1 |
| 2003/0091568 | A1 | 5/2003 | Frey | |
| 2004/0049022 | A1 * | 3/2004 | Nyce et al. | 536/23.2 |
| 2007/0299057 | A9 | 12/2007 | Ko et al. | |
| 2012/0052487 | A9 * | 3/2012 | Khvorova et al. | 435/6.1 |

OTHER PUBLICATIONS

Richards et al (J. Med. Chem. 2004, 47, 6451-6454).*
Santa Cruz Biotechnology, Inc. CD23 siRNA (h): sc-29976. (Sep. 13, 2007). [Retrieved from the Internet Aug. 13, 2009 at <http://datasheets.scbt.com/sc-29976.pdf>].

* cited by examiner

*Primary Examiner* — Richard Schnizer
(74) *Attorney, Agent, or Firm* — Dann Dorfman Herrell & Skillman; Kathleen D. Rigaut

(57) ABSTRACT

The present invention provides compositions and methods for the treatment of asthma. The compositions can be, for example, siRNA directed to CD23. The invention also provides a method of treating asthma with a formulation for in vivo delivery of a CD23 siRNA to inhibit IgE binding in a patient.

9 Claims, 8 Drawing Sheets

Figure 1:
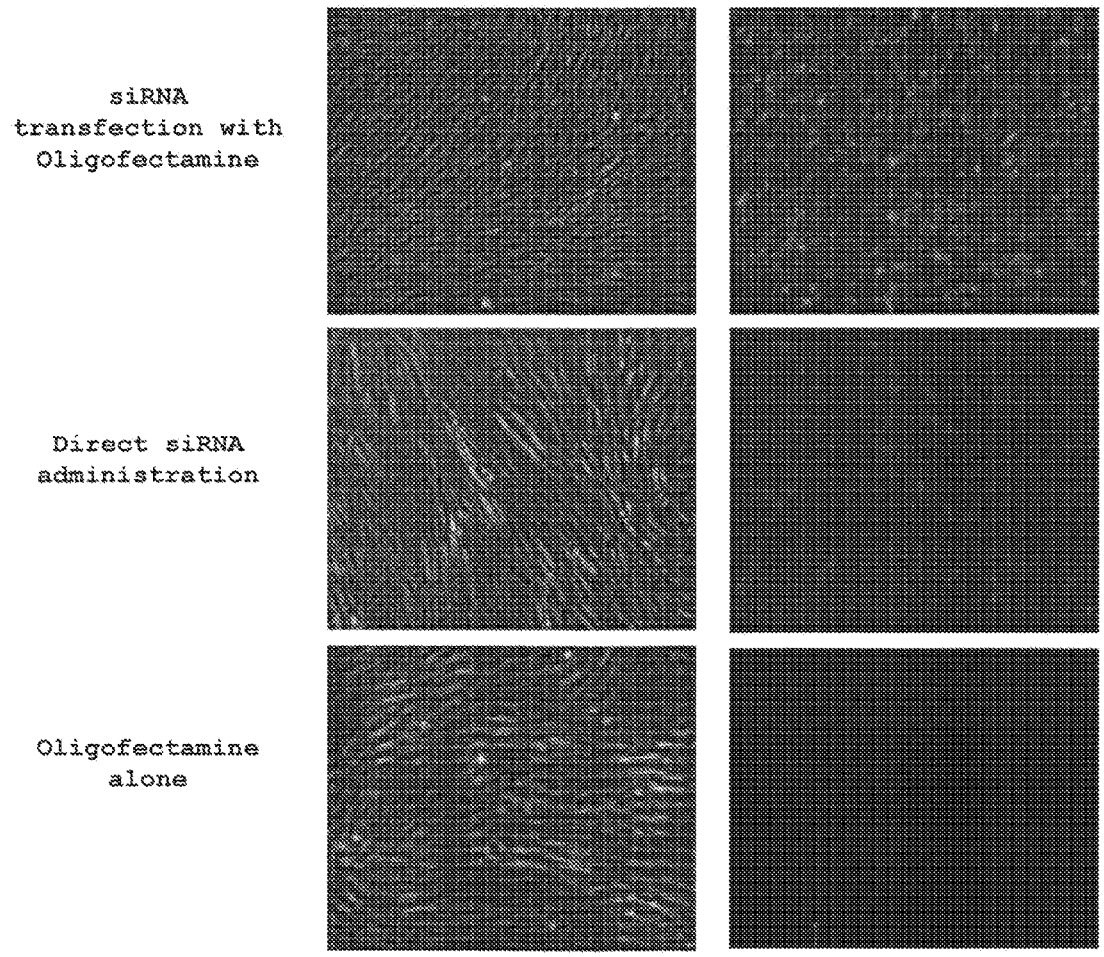

Efficiency assessment of human ASM cell transfection with a control fluorescin Cy™3-labeled siRNA duplexes Inhibition of CD23a mRNA expression in ASM cells following Oligofectamine-mediated transfection with CD23 siRNAs CD23 siRNA inhibits pro-asthmatic
changes in ASM tissue responsiveness

Figure 8

Sequence information for CD23

A) Nucleic Acid (SEQ ID NO: 1)

atggaggaaggtcaatattcagagatcgaggagcttcccaggaggcggtgttgcaggcgt
gggactcagatcgtgctgctggggctggtgaccgccgctctgtgggctgggctgctgact
ctgcttctcctgtggcactgggacaccacacagagtctaaaacagctggaagagagggct
gcccggaacgtctctcaagtttccaagaacttggaaagccaccacggtgaccagatggcg
cagaaatcccagtccacgcagatttcacaggaactggaggaacttcgagctgaacagcag
agattgaaatctcaggacttggagctgtcctggaacctgaacgggcttcaagcagatctg
agcagcttcaagtcccaggaattgaacgagaggaacgaagcttcagatttgctggaaaga
ctccgggaggaggtgacaaagctaaggatggagttgcaggtgtccagcggctttgtgtgc
aacacgtgccctgaaaagtggatcaatttccaacggaagtgctactacttcggcaagggc
accaagcagtgggtccacgcccggtatgcctgtgacgacatggaagggcagctggtcagc
atccacagcccggaggagcaggacttcctgaccaagcatgccagccacaccggctcctgg
attggccttcggaacttggacctgaaggggggagtttatctgggtggatgggagccacgtg
gactacagcaactgggctccaggggagcccaccagccggagccagggcgaggactgcgtg
atgatgcggggctccggtcgctggaacgacgccttctgcgaccgtaagctgggcgcctgg
gtgtgcgaccggctggccacatgcacgccgccagccagcgaaggttccgcggagtccatg
ggacctgattcaagaccagaccctgacggccgcctgcccaccccctctgcccctctccac
tcttga

B) Protein (SEQ ID NO: 2)

MEEGQYSEIEELPRRRCCRRGTQIVLLGLVTAALWAGLLTLLLL
WHWDTTQSLKQLEERAARNVSQVSKNLESHHGDQMAQKSQSTQI
SQELEELRAEQQRLKSQDLELSWNLNGLQADLSSFKSQELNERN
EASDLLERLREEVTKLRMELQVSSGFVCNTCPEKWINFQRKCYY
FGKGTKQWVHARYACDDMEGQLVSIHSPEEQDFLTKHASHTGSW
IGLRNLDLKGEFIWVDGSHVDYSNWAPGEPTSRSQGEDCVMMRG
SGRWNDAFCDRKLGAWVCDRLATCTPPASEGSAESMGPDSRPDP
DGRLPTPSAPLHS

SEQUENCE LISTING

<160> NUMBER OF SEQ ID NOS: 247

<210> SEQ ID NO 1
<211> LENGTH: 966
<212> TYPE: DNA
<213> ORGANISM: homo sapiens

<400> SEQUENCE: 1

```
atggaggaag gtcaatattc agagatcgag gagcttccca ggaggcggtg ttgcaggcgt      60
gggactcaga tcgtgctgct ggggctggtg accgccgctc tgtgggctgg gctgctgact     120
ctgcttctcc tgtggcactg ggacaccaca cagagtctaa aacagctgga agagagggct     180
gcccggaacg tctctcaagt ttccaagaac ttggaaagcc accacggtga ccagatggcg     240
cagaaatccc agtccacgca gatttcacag gaactggagg aacttcgagc tgaacagcag     300
agattgaaat ctcaggactt ggagctgtcc tggaacctga acgggcttca agcagatctg     360
agcagcttca gtcccagga attgaacgag aggaacgaag cttcagattt gctggaaaga     420
ctccgggagg aggtgacaaa gctaaggatg gagttgcagg tgtccagcgg ctttgtgtgc     480
aacacgtgcc ctgaaaagtg gatcaatttc caacggaagt gctactactt cggcaagggc     540
accaagcagt gggtccacgc ccggtatgcc tgtgacgaca tggaagggca gctggtcagc     600
atccacagcc cggaggagca ggacttcctg accaagcatg ccagccacac cggctcctgg     660
attggccttc ggaacttgga cctgaagggg gagtttatct gggtggatgg gagccacgtg     720
gactacagca actgggctcc aggggagccc accagccgga gccagggcga ggactgcgtg     780
atgatgcggg gctccggtcg ctggaacgac gccttctgcg accgtaagct gggcgcctgg     840
gtgtgcgacc ggctggccac atgcacgccg ccagccagcg aaggttccgc ggagtccatg     900
ggacctgatt caagaccaga ccctgacggc cgcctgccca ccccctctgc ccctctccac     960
tcttga                                                               966
```

<210> SEQ ID NO 2
<211> LENGTH: 642
<212> TYPE: PRT
<213> ORGANISM: homo sapiens

<400> SEQUENCE: 2

```
Met Glu Glu Gly Gln Tyr Ser Glu Ile Glu Glu Leu Pro Arg Arg Arg
 1               5                  10                  15

Cys Cys Arg Arg Gly Thr Gln Ile Val Leu Leu Gly Leu Val Thr Ala
            20                  25                  30

Ala Leu Trp Ala Gly Leu Leu Thr Leu Leu Leu Leu Trp His Trp Asp
        35                  40                  45
```

```
Thr Thr Gln Ser Leu Lys Gln Leu Glu Glu Arg Ala Ala Arg Asn Val
 50              55                  60
Ser Gln Val Ser Lys Asn Leu Glu Ser His His Gly Asp Gln Met Ala
 65              70                  75                  80
Gln Lys Ser Gln Ser Thr Gln Ile Ser Gln Glu Leu Glu Glu Leu Arg
                 85                  90                  95
Ala Glu Gln Gln Arg Leu Lys Ser Gln Asp Leu Glu Leu Ser Trp Asn
            100                 105                 110
Leu Asn Gly Leu Gln Ala Asp Leu Ser Ser Phe Lys Ser Gln Glu Leu
            115                 120                 125
Asn Glu Arg Asn Glu Ala Ser Asp Leu Leu Glu Arg Leu Arg Glu Glu
            130                 135                 140
Val Thr Lys Leu Arg Met Glu Leu Gln Val Ser Ser Gly Phe Val Cys
145                 150                 155                 160
Asn Thr Cys Pro Glu Lys Trp Ile Asn Phe Gln Arg Lys Cys Tyr Tyr
                165                 170                 175
Phe Gly Lys Gly Thr Lys Gln Trp Val His Ala Arg Tyr Ala Cys Asp
                180                 185                 190
Asp Met Glu Gly Gln Leu Val Ser Ile His Ser Pro Glu Glu Gln Asp
                195                 200                 205
Phe Leu Thr Lys His Ala Ser His Thr Gly Ser Trp Ile Gly Leu Arg
            210                 215                 220
Asn Leu Asp Leu Lys Gly Glu Phe Ile Trp Val Asp Gly Ser His Val
225                 230                 235                 240
Asp Tyr Ser Asn Trp Ala Pro Gly Glu Pro Thr Ser Arg Ser Gln Gly
                245                 250                 255
Glu Asp Cys Val Met Met Arg Gly Ser Gly Arg Trp Asn Asp Ala Phe
                260                 265                 270
Cys Asp Arg Lys Leu Gly Ala Trp Val Cys Asp Arg Leu Ala Thr Cys
            275                 280                 285
Thr Pro Pro Ala Ser Glu Gly Ser Ala Glu Ser Met Gly Pro Asp Ser
            290                 295                 300
Arg Pro Asp Pro Asp Gly Arg Leu Pro Thr Pro Ser Ala Pro Leu His
305                 310                 315                 320
Ser Met Glu Glu Gly Gln Tyr Ser Glu Ile Glu Glu Leu Pro Arg Arg
                325                 330                 335
Arg Cys Cys Arg Arg Gly Thr Gln Ile Val Leu Leu Gly Leu Val Thr
                340                 345                 350
Ala Ala Leu Trp Ala Gly Leu Leu Thr Leu Leu Leu Trp His Trp
            355                 360                 365
Asp Thr Thr Gln Ser Leu Lys Gln Leu Glu Glu Arg Ala Ala Arg Asn
            370                 375                 380
Val Ser Gln Val Ser Lys Asn Leu Glu Ser His His Gly Asp Gln Met
385                 390                 395                 400
Ala Gln Lys Ser Gln Ser Thr Gln Ile Ser Gln Glu Leu Glu Glu Leu
                405                 410                 415
Arg Ala Glu Gln Gln Arg Leu Lys Ser Gln Asp Leu Glu Leu Ser Trp
                420                 425                 430
Asn Leu Asn Gly Leu Gln Ala Asp Leu Ser Ser Phe Lys Ser Gln Glu
            435                 440                 445
Leu Asn Glu Arg Asn Glu Ala Ser Asp Leu Leu Glu Arg Leu Arg Glu
            450                 455                 460
Glu Val Thr Lys Leu Arg Met Glu Leu Gln Val Ser Ser Gly Phe Val
465                 470                 475                 480
```

```
Cys Asn Thr Cys Pro Glu Lys Trp Ile Asn Phe Gln Arg Lys Cys Tyr
                485                 490                 495

Tyr Phe Gly Lys Gly Thr Lys Gln Trp Val His Ala Arg Tyr Ala Cys
                500                 505                 510

Asp Asp Met Glu Gly Gln Leu Val Ser Ile His Ser Pro Glu Glu Gln
                515                 520                 525

Asp Phe Leu Thr Lys His Ala Ser His Thr Gly Ser Trp Ile Gly Leu
                530                 535                 540

Arg Asn Leu Asp Leu Lys Gly Glu Phe Ile Trp Val Asp Gly Ser His
545                 550                 555                 560

Val Asp Tyr Ser Asn Trp Ala Pro Gly Glu Pro Thr Ser Arg Ser Gln
                565                 570                 575

Gly Glu Asp Cys Val Met Met Arg Gly Ser Gly Arg Trp Asn Asp Ala
                580                 585                 590

Phe Cys Asp Arg Lys Leu Gly Ala Trp Val Cys Asp Arg Leu Ala Thr
                595                 600                 605

Cys Thr Pro Pro Ala Ser Glu Gly Ser Ala Glu Ser Met Gly Pro Asp
                610                 615                 620

Ser Arg Pro Asp Pro Asp Gly Arg Leu Pro Thr Pro Ser Ala Pro Leu
625                 630                 635                 640

His Ser

<210> SEQ ID NO 3
<211> LENGTH: 21
<212> TYPE: DNA
<213> ORGANISM: Artificial Sequence
<220> FEATURE:
<223> OTHER INFORMATION: siRNA

<400> SEQUENCE: 3
cgaagcuuca gauuugcugt t                                           21

<210> SEQ ID NO 4
<211> LENGTH: 21
<212> TYPE: DNA
<213> ORGANISM: Artificial Sequence
<220> FEATURE:
<223> OTHER INFORMATION: siRNA

<400> SEQUENCE: 4
cagcaaaucu gaagcuucgt t                                           21

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
ggugacaaag cuaaggaugt t                                           21

<210> SEQ ID NO 6
<211> LENGTH: 21
<212> TYPE: DNA
<213> ORGANISM: Artificial Sequence
<220> FEATURE:
<223> OTHER INFORMATION: siRNA

<400> SEQUENCE: 6
cauccuuagc uuugucacct c                                           21
```

<210> SEQ ID NO 7
<211> LENGTH: 21
<212> TYPE: DNA
<213> ORGANISM: Artificial Sequence
<220> FEATURE:
<223> OTHER INFORMATION: siRNA

<400> SEQUENCE: 7
ggaauugaac gagaggaact t                                    21

<210> SEQ ID NO 8
<211> LENGTH: 21
<212> TYPE: DNA
<213> ORGANISM: Artificial Sequence
<220> FEATURE:
<223> OTHER INFORMATION: siRNA

<400> SEQUENCE: 8 guccucucg uucaauucct g                                     21

<210> SEQ ID NO 9
<211> LENGTH: 21
<212> TYPE: DNA
<213> ORGANISM: Artificial Sequence
<220> FEATURE:
<223> OTHER INFORMATION: siRNA

<400> SEQUENCE: 9
ggaggugaca aagcuaaggt t                                    21

<210> SEQ ID NO 10
<211> LENGTH: 21
<212> TYPE: DNA
<213> ORGANISM: Artificial Sequence
<220> FEATURE:
<223> OTHER INFORMATION: siRNA

<400> SEQUENCE: 10
ccuuagcuuu gucaccucct c                                    21

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
cacaatggag gaaggtcaat attcag                               26

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
ttgagagacg ttccgggcag ccctctcttc cagctgtt                  38

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gagaagagct acgagctgcc tgac                                              24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
cggagtactt gcgctcagga ggag                                              24

<210> SEQ ID NO 15
<211> LENGTH: 22
<212> TYPE: DNA
<213> ORGANISM: Artificial Sequence
<220> FEATURE:
<223> OTHER INFORMATION: shRNA

<400> SEQUENCE: 15
cgctgaacag cagagattga aa                                                22

<210> SEQ ID NO 16
<211> LENGTH: 22
<212> TYPE: DNA
<213> ORGANISM: Artificial Sequence
<220> FEATURE:
<223> OTHER INFORMATION: shRNA

<400> SEQUENCE: 16
cccacggatg cggccccgtg cc                                                22

<210> SEQ ID NO 17
<211> LENGTH: 21
<212> TYPE: DNA
<213> ORGANISM: Artificial Sequence
<220> FEATURE:
<223> OTHER INFORMATION: siRNA

<400> SEQUENCE: 17
ggucaauauu cagagaucgt t                                                 21

<210> SEQ ID NO 18
<211> LENGTH: 21
<212> TYPE: DNA
<213> ORGANISM: Artificial Sequence
<220> FEATURE:
<223> OTHER INFORMATION: siRNA

<400> SEQUENCE: 18
cgaucucuga auauugacct t                                                 21

<210> SEQ ID NO 19
<211> LENGTH: 21
<212> TYPE: DNA
<213> ORGANISM: Artificial Sequence
<220> FEATURE:
<223> OTHER INFORMATION: siRNA

<400> SEQUENCE: 19
uauucagaga ucgaggagct t                                                 21

<210> SEQ ID NO 20
<211> LENGTH: 21

```
<212> TYPE: DNA
<213> ORGANISM: Artificial Sequence
<220> FEATURE:
<223> OTHER INFORMATION: siRNA

<400> SEQUENCE: 20
gcuccucgau cucugaauat t                                              21

<210> SEQ ID NO 21
<211> LENGTH: 21
<212> TYPE: DNA
<213> ORGANISM: Artificial Sequence
<220> FEATURE:
<223> OTHER INFORMATION: siRNA

<400> SEQUENCE: 21
aacagcugga agagagggct t                                              21

<210> SEQ ID NO 22
<211> LENGTH: 21
<212> TYPE: DNA
<213> ORGANISM: Artificial Sequence
<220> FEATURE:
<223> OTHER INFORMATION: siRNA

<400> SEQUENCE: 22
gcccucucuu ccagcuguut t                                              21

<210> SEQ ID NO 23
<211> LENGTH: 21
<212> TYPE: DNA
<213> ORGANISM: Artificial Sequence
<220> FEATURE:
<223> OTHER INFORMATION: siRNA

<400> SEQUENCE: 23
cagcuggaag agagggcugt t                                              21

<210> SEQ ID NO 24
<211> LENGTH: 21
<212> TYPE: DNA
<213> ORGANISM: Artificial Sequence
<220> FEATURE:
<223> OTHER INFORMATION: siRNA

<400> SEQUENCE: 24
cagcccucuc uuccagcugt t                                              21

<210> SEQ ID NO 25
<211> LENGTH: 21
<212> TYPE: DNA
<213> ORGANISM: Artificial Sequence
<220> FEATURE:
<223> OTHER INFORMATION: siRNA

<400> SEQUENCE: 25
gagagggcug cccggaacgt t                                              21

<210> SEQ ID NO 26
<211> LENGTH: 21
<212> TYPE: DNA
<213> ORGANISM: Artificial Sequence
<220> FEATURE:
<223> OTHER INFORMATION: siRNA

<400> SEQUENCE: 26
cguuccgggc agcccucuct t                                              21
```

<210> SEQ ID NO 27
<211> LENGTH: 21
<212> TYPE: DNA
<213> ORGANISM: Artificial Sequence
<220> FEATURE:
<223> OTHER INFORMATION: siRNA

<400> SEQUENCE: 27
cgucucucaa guuuccaagt t                                              21

<210> SEQ ID NO 28
<211> LENGTH: 21
<212> TYPE: DNA
<213> ORGANISM: Artificial Sequence
<220> FEATURE:
<223> OTHER INFORMATION: siRNA

<400> SEQUENCE: 28
cuuggaaacu ugagagacgt t                                              21

<210> SEQ ID NO 29
<211> LENGTH: 21
<212> TYPE: DNA
<213> ORGANISM: Artificial Sequence
<220> FEATURE:
<223> OTHER INFORMATION: siRNA

<400> SEQUENCE: 29
guuuccaaga acuuggaaat t                                              21

<210> SEQ ID NO 30
<211> LENGTH: 21
<212> TYPE: DNA
<213> ORGANISM: Artificial Sequence
<220> FEATURE:
<223> OTHER INFORMATION: siRNA

<400> SEQUENCE: 30
uuuccaaguu cuuggaaact t                                              21

<210> SEQ ID NO 31
<211> LENGTH: 21
<212> TYPE: DNA
<213> ORGANISM: Artificial Sequence
<220> FEATURE:
<223> OTHER INFORMATION: siRNA

<400> SEQUENCE: 31
gaacuuggaa agccaccact t                                              21

<210> SEQ ID NO 32
<211> LENGTH: 21
<212> TYPE: DNA
<213> ORGANISM: Artificial Sequence
<220> FEATURE:
<223> OTHER INFORMATION: siRNA

<400> SEQUENCE: 32
gaacuuggaa agccaccact t                                              21

<210> SEQ ID NO 33
<211> LENGTH: 21
<212> TYPE: DNA
<213> ORGANISM: Artificial Sequence
<220> FEATURE:
<223> OTHER INFORMATION: siRNA

```
<400> SEQUENCE: 33
cuuggaaagc caccacggut t                                              21

<210> SEQ ID NO 34
<211> LENGTH: 21
<212> TYPE: DNA
<213> ORGANISM: Artificial Sequence
<220> FEATURE:
<223> OTHER INFORMATION: siRNA

<400> SEQUENCE: 34 accgugugg cuuccaagt t                                                21

<210> SEQ ID NO 35
<211> LENGTH: 21
<212> TYPE: DNA
<213> ORGANISM: Artificial Sequence
<220> FEATURE:
<223> OTHER INFORMATION: siRNA

<400> SEQUENCE: 35
agccaccacg gugaccagat t                                              21

<210> SEQ ID NO 36
<211> LENGTH: 21
<212> TYPE: DNA
<213> ORGANISM: Artificial Sequence
<220> FEATURE:
<223> OTHER INFORMATION: siRNA

<400> SEQUENCE: 36
ucuggucacc gugguggcut t                                              21

<210> SEQ ID NO 37
<211> LENGTH: 21
<212> TYPE: DNA
<213> ORGANISM: Artificial Sequence
<220> FEATURE:
<223> OTHER INFORMATION: siRNA

<400> SEQUENCE: 37
aucccagucc acgcagauut t                                              21

<210> SEQ ID NO 38
<211> LENGTH: 21
<212> TYPE: DNA
<213> ORGANISM: Artificial Sequence
<220> FEATURE:
<223> OTHER INFORMATION: siRNA

<400> SEQUENCE: 38
aaucugcgug gacugggaut t                                              21

<210> SEQ ID NO 39
<211> LENGTH: 21
<212> TYPE: DNA
<213> ORGANISM: Artificial Sequence
<220> FEATURE:
<223> OTHER INFORMATION: siRNA

<400> SEQUENCE: 39
cuggaggaac uucgagcugt t                                              21

<210> SEQ ID NO 40
<211> LENGTH: 21
```

```
<212> TYPE: DNA
<213> ORGANISM: Artificial Sequence
<220> FEATURE:
<223> OTHER INFORMATION: siRNA

<400> SEQUENCE: 40
cagcucgaag uuccuccagt t                                              21

<210> SEQ ID NO 41
<211> LENGTH: 21
<212> TYPE: DNA
<213> ORGANISM: Artificial Sequence
<220> FEATURE:
<223> OTHER INFORMATION: siRNA

<400> SEQUENCE: 41
cuucgagcug aacagcagat t                                              21

<210> SEQ ID NO 42
<211> LENGTH: 21
<212> TYPE: DNA
<213> ORGANISM: Artificial Sequence
<220> FEATURE:
<223> OTHER INFORMATION: siRNA

<400> SEQUENCE: 42
ucugcuguuc agcucgaagt t                                              21

<210> SEQ ID NO 43
<211> LENGTH: 21
<212> TYPE: DNA
<213> ORGANISM: Artificial Sequence
<220> FEATURE:
<223> OTHER INFORMATION: siRNA

<400> SEQUENCE: 43
cagcagagau ugaaaucuct t                                              21

<210> SEQ ID NO 44
<211> LENGTH: 21
<212> TYPE: DNA
<213> ORGANISM: Artificial Sequence
<220> FEATURE:
<223> OTHER INFORMATION: siRNA

<400> SEQUENCE: 44
gagauuucaa ucucugcugt t                                              21

<210> SEQ ID NO 45
<211> LENGTH: 21
<212> TYPE: DNA
<213> ORGANISM: Artificial Sequence
<220> FEATURE:
<223> OTHER INFORMATION: siRNA

<400> SEQUENCE: 45
aucucaggac uuggagcugt t                                              21

<210> SEQ ID NO 46
<211> LENGTH: 21
<212> TYPE: DNA
<213> ORGANISM: Artificial Sequence
<220> FEATURE:
<223> OTHER INFORMATION: siRNA

<400> SEQUENCE: 46
cagcuccaag uccugagaut t                                              21
```

<210> SEQ ID NO 47
<211> LENGTH: 21
<212> TYPE: DNA
<213> ORGANISM: Artificial Sequence
<220> FEATURE:
<223> OTHER INFORMATION: siRNA

<400> SEQUENCE: 47
ccugaacggg cuucaagcat t                                             21

<210> SEQ ID NO 48
<211> LENGTH: 21
<212> TYPE: DNA
<213> ORGANISM: Artificial Sequence
<220> FEATURE:
<223> OTHER INFORMATION: siRNA

<400> SEQUENCE: 48
ugcuugaagc ccguucaggt t                                             21

<210> SEQ ID NO 49
<211> LENGTH: 21
<212> TYPE: DNA
<213> ORGANISM: Artificial Sequence
<220> FEATURE:
<223> OTHER INFORMATION: siRNA

<400> SEQUENCE: 49
cgggcuucaa gcagaucugt t                                             21

<210> SEQ ID NO 50
<211> LENGTH: 21
<212> TYPE: DNA
<213> ORGANISM: Artificial Sequence
<220> FEATURE:
<223> OTHER INFORMATION: siRNA

<400> SEQUENCE: 50
cagaucugcu ugaagcccgt t                                             21

<210> SEQ ID NO 51
<211> LENGTH: 21
<212> TYPE: DNA
<213> ORGANISM: Artificial Sequence
<220> FEATURE:
<223> OTHER INFORMATION: siRNA

<400> SEQUENCE: 51
gcagaucuga gcagcuucat t                                             21

<210> SEQ ID NO 52
<211> LENGTH: 21
<212> TYPE: DNA
<213> ORGANISM: Artificial Sequence
<220> FEATURE:
<223> OTHER INFORMATION: siRNA

<400> SEQUENCE: 52
ugaagcugcu cagaucugct t                                             21

<210> SEQ ID NO 53
<211> LENGTH: 21
<212> TYPE: DNA
<213> ORGANISM: Artificial Sequence
<220> FEATURE:
<223> OTHER INFORMATION: siRNA

```
<400> SEQUENCE: 53
gucccaggaa uugaacgagt t                                              21

<210> SEQ ID NO 54
<211> LENGTH: 21
<212> TYPE: DNA
<213> ORGANISM: Artificial Sequence
<220> FEATURE:
<223> OTHER INFORMATION: siRNA

<400> SEQUENCE: 54
cucguucaau uccugggact t                                              21

<210> SEQ ID NO 55
<211> LENGTH: 21
<212> TYPE: DNA
<213> ORGANISM: Artificial Sequence
<220> FEATURE:
<223> OTHER INFORMATION: siRNA

<400> SEQUENCE: 55
uugaacgaga ggaacgaagt t                                              21

<210> SEQ ID NO 56
<211> LENGTH: 21
<212> TYPE: DNA
<213> ORGANISM: Artificial Sequence
<220> FEATURE:
<223> OTHER INFORMATION: siRNA

<400> SEQUENCE: 56
cuucguuccu cucguucaat t                                              21

<210> SEQ ID NO 57
<211> LENGTH: 21
<212> TYPE: DNA
<213> ORGANISM: Artificial Sequence
<220> FEATURE:
<223> OTHER INFORMATION: siRNA

<400> SEQUENCE: 57
cgagaggaac gaagcuucat t                                              21

<210> SEQ ID NO 58
<211> LENGTH: 21
<212> TYPE: DNA
<213> ORGANISM: Artificial Sequence
<220> FEATURE:
<223> OTHER INFORMATION: siRNA

<400> SEQUENCE: 58
ugaagcuucg uuccucucgt t                                              21

<210> SEQ ID NO 59
<211> LENGTH: 21
<212> TYPE: DNA
<213> ORGANISM: Artificial Sequence
<220> FEATURE:
<223> OTHER INFORMATION: siRNA

<400> SEQUENCE: 59
gcuucagauu ugcuggaaat t                                              21

<210> SEQ ID NO 60
<211> LENGTH: 21
```

-continued

```
<212> TYPE: DNA
<213> ORGANISM: Artificial Sequence
<220> FEATURE:
<223> OTHER INFORMATION: siRNA

<400> SEQUENCE: 60
uuuccagcaa aucugaagct t                                                 21

<210> SEQ ID NO 61
<211> LENGTH: 21
<212> TYPE: DNA
<213> ORGANISM: Artificial Sequence
<220> FEATURE:
<223> OTHER INFORMATION: siRNA

<400> SEQUENCE: 61
agacuccggg aggaggugat t                                                 21

<210> SEQ ID NO 62
<211> LENGTH: 21
<212> TYPE: DNA
<213> ORGANISM: Artificial Sequence
<220> FEATURE:
<223> OTHER INFORMATION: siRNA

<400> SEQUENCE: 62
ucaccuccuc ccggagucut t                                                 21

<210> SEQ ID NO 63
<211> LENGTH: 21
<212> TYPE: DNA
<213> ORGANISM: Artificial Sequence
<220> FEATURE:
<223> OTHER INFORMATION: siRNA

<400> SEQUENCE: 63
agcuaaggau ggaguugcat t                                                 21

<210> SEQ ID NO 64
<211> LENGTH: 21
<212> TYPE: DNA
<213> ORGANISM: Artificial Sequence
<220> FEATURE:
<223> OTHER INFORMATION: siRNA

<400> SEQUENCE: 64
ugcaacucca uccuuagcut t                                                 21

<210> SEQ ID NO 65
<211> LENGTH: 21
<212> TYPE: DNA
<213> ORGANISM: Artificial Sequence
<220> FEATURE:
<223> OTHER INFORMATION: siRNA

<400> SEQUENCE: 65
ggauggaguu gcagguguct t                                                 21

<210> SEQ ID NO 66
<211> LENGTH: 21
<212> TYPE: DNA
<213> ORGANISM: Artificial Sequence
<220> FEATURE:
<223> OTHER INFORMATION: siRNA

<400> SEQUENCE: 66
gacaccugca acuccaucct t                                                 21
```

```
<210> SEQ ID NO 67
<211> LENGTH: 21
<212> TYPE: DNA
<213> ORGANISM: Artificial Sequence
<220> FEATURE:
<223> OTHER INFORMATION: siRNA

<400> SEQUENCE: 67
cacgugcccu gaaaaguggt t                                              21

<210> SEQ ID NO 68
<211> LENGTH: 21
<212> TYPE: DNA
<213> ORGANISM: Artificial Sequence
<220> FEATURE:
<223> OTHER INFORMATION: siRNA

<400> SEQUENCE: 68
ccacuuuuca gggcacgugt t                                              21

<210> SEQ ID NO 69
<211> LENGTH: 21
<212> TYPE: DNA
<213> ORGANISM: Artificial Sequence
<220> FEATURE:
<223> OTHER INFORMATION: siRNA

<400> SEQUENCE: 69
aaguggauca auuccaact t                                               21

<210> SEQ ID NO 70
<211> LENGTH: 21
<212> TYPE: DNA
<213> ORGANISM: Artificial Sequence
<220> FEATURE:
<223> OTHER INFORMATION: siRNA

<400> SEQUENCE: 70
guuggaaauu gauccacuut t                                              21

<210> SEQ ID NO 71
<211> LENGTH: 21
<212> TYPE: DNA
<213> ORGANISM: Artificial Sequence
<220> FEATURE:
<223> OTHER INFORMATION: siRNA

<400> SEQUENCE: 71
guggaucaau uuccaacggt t                                              21

<210> SEQ ID NO 72
<211> LENGTH: 21
<212> TYPE: DNA
<213> ORGANISM: Artificial Sequence
<220> FEATURE:
<223> OTHER INFORMATION: siRNA

<400> SEQUENCE: 72
ccguuggaaa uugauccact t                                              21

<210> SEQ ID NO 73
<211> LENGTH: 21
<212> TYPE: DNA
<213> ORGANISM: Artificial Sequence
<220> FEATURE:
<223> OTHER INFORMATION: siRNA
```

```
<400> SEQUENCE: 73
uuuccaacgg aagugcuact t                                              21

<210> SEQ ID NO 74
<211> LENGTH: 21
<212> TYPE: DNA
<213> ORGANISM: Artificial Sequence
<220> FEATURE:
<223> OTHER INFORMATION: siRNA

<400> SEQUENCE: 74
guagcacuuc cguuggaaat t                                              21

<210> SEQ ID NO 75
<211> LENGTH: 21
<212> TYPE: DNA
<213> ORGANISM: Artificial Sequence
<220> FEATURE:
<223> OTHER INFORMATION: siRNA

<400> SEQUENCE: 75
cggaagugcu acuacuucgt t                                              21

<210> SEQ ID NO 76
<211> LENGTH: 21
<212> TYPE: DNA
<213> ORGANISM: Artificial Sequence
<220> FEATURE:
<223> OTHER INFORMATION: siRNA

<400> SEQUENCE: 76
cgaaguagua gcacuuccgt t                                              21

<210> SEQ ID NO 77
<211> LENGTH: 21
<212> TYPE: DNA
<213> ORGANISM: Artificial Sequence
<220> FEATURE:
<223> OTHER INFORMATION: siRNA

<400> SEQUENCE: 77
gugcuacuac uucggcaagt t                                              21

<210> SEQ ID NO 78
<211> LENGTH: 21
<212> TYPE: DNA
<213> ORGANISM: Artificial Sequence
<220> FEATURE:
<223> OTHER INFORMATION: siRNA

<400> SEQUENCE: 78
cuugccgaag uaguagcact t                                              21

<210> SEQ ID NO 79
<211> LENGTH: 21
<212> TYPE: DNA
<213> ORGANISM: Artificial Sequence
<220> FEATURE:
<223> OTHER INFORMATION: siRNA

<400> SEQUENCE: 79
gggcaccaag caguggguct t                                              21

<210> SEQ ID NO 80
<211> LENGTH: 21
```

<212> TYPE: DNA
<213> ORGANISM: Artificial Sequence
<220> FEATURE:
<223> OTHER INFORMATION: siRNA

<400> SEQUENCE: 80
gacccacugc uuggugccct t                                            21

<210> SEQ ID NO 81
<211> LENGTH: 21
<212> TYPE: DNA
<213> ORGANISM: Artificial Sequence
<220> FEATURE:
<223> OTHER INFORMATION: siRNA

<400> SEQUENCE: 81
gcaguggguc cacgcccggt t                                            21

<210> SEQ ID NO 82
<211> LENGTH: 21
<212> TYPE: DNA
<213> ORGANISM: Artificial Sequence
<220> FEATURE:
<223> OTHER INFORMATION: siRNA

<400> SEQUENCE: 82
ccgggcgugg acccacugct t                                            21

<210> SEQ ID NO 83
<211> LENGTH: 21
<212> TYPE: DNA
<213> ORGANISM: Artificial Sequence
<220> FEATURE:
<223> OTHER INFORMATION: siRNA

<400> SEQUENCE: 83
gggcagcugg ucagcaucct t                                            21

<210> SEQ ID NO 84
<211> LENGTH: 21
<212> TYPE: DNA
<213> ORGANISM: Artificial Sequence
<220> FEATURE:
<223> OTHER INFORMATION: siRNA

<400> SEQUENCE: 84
ggaugcugac cagcugccct t                                            21

<210> SEQ ID NO 85
<211> LENGTH: 21
<212> TYPE: DNA
<213> ORGANISM: Artificial Sequence
<220> FEATURE:
<223> OTHER INFORMATION: siRNA

<400> SEQUENCE: 85
gcaugccagc cacaccggct t                                            21

<210> SEQ ID NO 86
<211> LENGTH: 21
<212> TYPE: DNA
<213> ORGANISM: Artificial Sequence
<220> FEATURE:
<223> OTHER INFORMATION: siRNA

<400> SEQUENCE: 86 gccgugugg cuggcaugct t                                             21

```
<210> SEQ ID NO 87
<211> LENGTH: 21
<212> TYPE: DNA
<213> ORGANISM: Artificial Sequence
<220> FEATURE:
<223> OTHER INFORMATION: siRNA

<400> SEQUENCE: 87
cuuggaccug aaggggagt t                                              21

<210> SEQ ID NO 88
<211> LENGTH: 21
<212> TYPE: DNA
<213> ORGANISM: Artificial Sequence
<220> FEATURE:
<223> OTHER INFORMATION: siRNA

<400> SEQUENCE: 88 cuccccuuc agguccaagt t                                              21

<210> SEQ ID NO 89
<211> LENGTH: 21
<212> TYPE: DNA
<213> ORGANISM: Artificial Sequence
<220> FEATURE:
<223> OTHER INFORMATION: siRNA

<400> SEQUENCE: 89
gggggaguuu aucugggugt t                                             21

<210> SEQ ID NO 90
<211> LENGTH: 21
<212> TYPE: DNA
<213> ORGANISM: Artificial Sequence
<220> FEATURE:
<223> OTHER INFORMATION: siRNA

<400> SEQUENCE: 90
cacccagaua aacucccct t                                              21

<210> SEQ ID NO 91
<211> LENGTH: 21
<212> TYPE: DNA
<213> ORGANISM: Artificial Sequence
<220> FEATURE:
<223> OTHER INFORMATION: siRNA

<400> SEQUENCE: 91
cugggcucca ggggagcccu t                                             21

<210> SEQ ID NO 92
<211> LENGTH: 21
<212> TYPE: DNA
<213> ORGANISM: Artificial Sequence
<220> FEATURE:
<223> OTHER INFORMATION: siRNA

<400> SEQUENCE: 92 gggcucccu ggagcccagt t                                              21

<210> SEQ ID NO 93
<211> LENGTH: 21
<212> TYPE: DNA
<213> ORGANISM: Artificial Sequence
<220> FEATURE:
<223> OTHER INFORMATION: siRNA
```

```
<400> SEQUENCE: 93
cgacgccuuc ugcgaccgut t                                              21

<210> SEQ ID NO 94
<211> LENGTH: 21
<212> TYPE: DNA
<213> ORGANISM: Artificial Sequence
<220> FEATURE:
<223> OTHER INFORMATION: siRNA

<400> SEQUENCE: 94
acggucgcag aaggcgucgt t                                              21

<210> SEQ ID NO 95
<211> LENGTH: 21
<212> TYPE: DNA
<213> ORGANISM: Artificial Sequence
<220> FEATURE:
<223> OTHER INFORMATION: siRNA

<400> SEQUENCE: 95
gcugggcgcc uggugugct t                                               21

<210> SEQ ID NO 96
<211> LENGTH: 21
<212> TYPE: DNA
<213> ORGANISM: Artificial Sequence
<220> FEATURE:
<223> OTHER INFORMATION: siRNA

<400> SEQUENCE: 96
gcacacccag gcgcccagct t                                              21

<210> SEQ ID NO 97
<211> LENGTH: 21
<212> TYPE: DNA
<213> ORGANISM: Artificial Sequence
<220> FEATURE:
<223> OTHER INFORMATION: siRNA

<400> SEQUENCE: 97
gguuccgcgg aguccauggt t                                              21

<210> SEQ ID NO 98
<211> LENGTH: 21
<212> TYPE: DNA
<213> ORGANISM: Artificial Sequence
<220> FEATURE:
<223> OTHER INFORMATION: siRNA

<400> SEQUENCE: 98
ccauggacuc cgcggaacct t                                              21

<210> SEQ ID NO 99
<211> LENGTH: 21
<212> TYPE: DNA
<213> ORGANISM: Artificial Sequence
<220> FEATURE:
<223> OTHER INFORMATION: siRNA

<400> SEQUENCE: 99
gaccagaccc ugacggccgt t                                              21

<210> SEQ ID NO 100
<211> LENGTH: 21
```

```
<212> TYPE: DNA
<213> ORGANISM: Artificial Sequence
<220> FEATURE:
<223> OTHER INFORMATION: siRNA

<400> SEQUENCE: 100
cggccgucag ggucuggguct t                                           21

<210> SEQ ID NO 101
<211> LENGTH: 21
<212> TYPE: DNA
<213> ORGANISM: Artificial Sequence
<220> FEATURE:
<223> OTHER INFORMATION: siRNA

<400> SEQUENCE: 101
ggctgggctg ctgactctgt t                                            21

<210> SEQ ID NO 102
<211> LENGTH: 21
<212> TYPE: DNA
<213> ORGANISM: Artificial Sequence
<220> FEATURE:
<223> OTHER INFORMATION: siRNA

<400> SEQUENCE: 102
gctgggctgc tgactctgct t                                            21

<210> SEQ ID NO 103
<211> LENGTH: 21
<212> TYPE: DNA
<213> ORGANISM: Artificial Sequence
<220> FEATURE:
<223> OTHER INFORMATION: siRNA

<400> SEQUENCE: 103
ctgggctgct gactctgctt t                                            21

<210> SEQ ID NO 104
<211> LENGTH: 21
<212> TYPE: DNA
<213> ORGANISM: Artificial Sequence
<220> FEATURE:
<223> OTHER INFORMATION: siRNA

<400> SEQUENCE: 104
gggctgctga ctctgcttct t                                            21

<210> SEQ ID NO 105
<211> LENGTH: 21
<212> TYPE: DNA
<213> ORGANISM: Artificial Sequence
<220> FEATURE:
<223> OTHER INFORMATION: siRNA

<400> SEQUENCE: 105
caccacacag agtctaaaat t                                            21

<210> SEQ ID NO 106
<211> LENGTH: 21
<212> TYPE: DNA
<213> ORGANISM: Artificial Sequence
<220> FEATURE:
<223> OTHER INFORMATION: siRNA

<400> SEQUENCE: 106
ccacacagag tctaaaacat t                                            21
```

<210> SEQ ID NO 107
<211> LENGTH: 21
<212> TYPE: DNA
<213> ORGANISM: Artificial Sequence
<220> FEATURE:
<223> OTHER INFORMATION: siRNA

<400> SEQUENCE: 107
cacagagtct aaaacagctt t                                          21

<210> SEQ ID NO 108
<211> LENGTH: 21
<212> TYPE: DNA
<213> ORGANISM: Artificial Sequence
<220> FEATURE:
<223> OTHER INFORMATION: siRNA

<400> SEQUENCE: 108
cagagtctaa aacagctggt t                                          21

<210> SEQ ID NO 109
<211> LENGTH: 21
<212> TYPE: DNA
<213> ORGANISM: Artificial Sequence
<220> FEATURE:
<223> OTHER INFORMATION: siRNA

<400> SEQUENCE: 109
gagtctaaaa cagctggaat t                                          21

<210> SEQ ID NO 110
<211> LENGTH: 21
<212> TYPE: DNA
<213> ORGANISM: Artificial Sequence
<220> FEATURE:
<223> OTHER INFORMATION: siRNA

<400> SEQUENCE: 110
gtctaaaaca gctggaagat t                                          21

<210> SEQ ID NO 111
<211> LENGTH: 21
<212> TYPE: DNA
<213> ORGANISM: Artificial Sequence
<220> FEATURE:
<223> OTHER INFORMATION: siRNA

<400> SEQUENCE: 111
aaacagctgg aagagagggt t                                          21

<210> SEQ ID NO 112
<211> LENGTH: 21
<212> TYPE: DNA
<213> ORGANISM: Artificial Sequence
<220> FEATURE:
<223> OTHER INFORMATION: siRNA

<400> SEQUENCE: 112
aacagctgga agagagggct t                                          21

<210> SEQ ID NO 113
<211> LENGTH: 21
<212> TYPE: DNA
<213> ORGANISM: Artificial Sequence
<220> FEATURE:
<223> OTHER INFORMATION: siRNA

<400> SEQUENCE: 113
acagctggaa gagagggctt t                                              21

<210> SEQ ID NO 114
<211> LENGTH: 21
<212> TYPE: DNA
<213> ORGANISM: Artificial Sequence
<220> FEATURE:
<223> OTHER INFORMATION: siRNA

<400> SEQUENCE: 114
cagctggaag agagggctgt t                                              21

<210> SEQ ID NO 115
<211> LENGTH: 21
<212> TYPE: DNA
<213> ORGANISM: Artificial Sequence
<220> FEATURE:
<223> OTHER INFORMATION: siRNA

<400> SEQUENCE: 115
agagagggct gcccggaact t                                              21

<210> SEQ ID NO 116
<211> LENGTH: 21
<212> TYPE: DNA
<213> ORGANISM: Artificial Sequence
<220> FEATURE:
<223> OTHER INFORMATION: siRNA

<400> SEQUENCE: 116
acgtctctca agtttccaat t                                              21

<210> SEQ ID NO 117
<211> LENGTH: 21
<212> TYPE: DNA
<213> ORGANISM: Artificial Sequence
<220> FEATURE:
<223> OTHER INFORMATION: siRNA

<400> SEQUENCE: 117
cgtctctcaa gtttccaagt t                                              21

<210> SEQ ID NO 118
<211> LENGTH: 21
<212> TYPE: DNA
<213> ORGANISM: Artificial Sequence
<220> FEATURE:
<223> OTHER INFORMATION: siRNA

<400> SEQUENCE: 118
agtttccaag aacttggaat t                                              21

<210> SEQ ID NO 119
<211> LENGTH: 21
<212> TYPE: DNA
<213> ORGANISM: Artificial Sequence
<220> FEATURE:
<223> OTHER INFORMATION: siRNA

<400> SEQUENCE: 119
gtttccaaga acttggaaat t                                              21

<210> SEQ ID NO 120
<211> LENGTH: 21

-continued

```
<212> TYPE: DNA
<213> ORGANISM: Artificial Sequence
<220> FEATURE:
<223> OTHER INFORMATION: siRNA

<400> SEQUENCE: 120
gtttccaaga acttggaaat t                                              21

<210> SEQ ID NO 121
<211> LENGTH: 21
<212> TYPE: DNA
<213> ORGANISM: Artificial Sequence
<220> FEATURE:
<223> OTHER INFORMATION: siRNA

<400> SEQUENCE: 121
gaacttggaa agccaccact t                                              21

<210> SEQ ID NO 122
<211> LENGTH: 21
<212> TYPE: DNA
<213> ORGANISM: Artificial Sequence
<220> FEATURE:
<223> OTHER INFORMATION: siRNA

<400> SEQUENCE: 122
acttggaaag ccaccacggt t                                              21

<210> SEQ ID NO 123
<211> LENGTH: 21
<212> TYPE: DNA
<213> ORGANISM: Artificial Sequence
<220> FEATURE:
<223> OTHER INFORMATION: siRNA

<400> SEQUENCE: 123
cttggaaagc caccacggtt t                                              21

<210> SEQ ID NO 124
<211> LENGTH: 21
<212> TYPE: DNA
<213> ORGANISM: Artificial Sequence
<220> FEATURE:
<223> OTHER INFORMATION: siRNA

<400> SEQUENCE: 124
aagccaccac ggtgaccagt t                                              21

<210> SEQ ID NO 125
<211> LENGTH: 21
<212> TYPE: DNA
<213> ORGANISM: Artificial Sequence
<220> FEATURE:
<223> OTHER INFORMATION: siRNA

<400> SEQUENCE: 125
agccaccacg gtgaccagat t                                              21

<210> SEQ ID NO 126
<211> LENGTH: 21
<212> TYPE: DNA
<213> ORGANISM: Artificial Sequence
<220> FEATURE:
<223> OTHER INFORMATION: siRNA

<400> SEQUENCE: 126
gccaccacgg tgaccagatt t                                              21
```

<210> SEQ ID NO 127
<211> LENGTH: 21
<212> TYPE: DNA
<213> ORGANISM: Artificial Sequence
<220> FEATURE:
<223> OTHER INFORMATION: siRNA

<400> SEQUENCE: 127
ccacggtgac cagatggcgt t                                      21

<210> SEQ ID NO 128
<211> LENGTH: 21
<212> TYPE: DNA
<213> ORGANISM: Artificial Sequence
<220> FEATURE:
<223> OTHER INFORMATION: siRNA

<400> SEQUENCE: 128
cggtgaccag atggcgcagt t                                      21

<210> SEQ ID NO 129
<211> LENGTH: 21
<212> TYPE: DNA
<213> ORGANISM: Artificial Sequence
<220> FEATURE:
<223> OTHER INFORMATION: siRNA

<400> SEQUENCE: 129
ccagatggcg cagaaatcct t                                      21

<210> SEQ ID NO 130
<211> LENGTH: 21
<212> TYPE: DNA
<213> ORGANISM: Artificial Sequence
<220> FEATURE:
<223> OTHER INFORMATION: siRNA

<400> SEQUENCE: 130
gatggcgcag aaatcccagt t                                      21

<210> SEQ ID NO 131
<211> LENGTH: 21
<212> TYPE: DNA
<213> ORGANISM: Artificial Sequence
<220> FEATURE:
<223> OTHER INFORMATION: siRNA

<400> SEQUENCE: 131
tggcgcagaa atcccagtct t                                      21

<210> SEQ ID NO 132
<211> LENGTH: 21
<212> TYPE: DNA
<213> ORGANISM: Artificial Sequence
<220> FEATURE:
<223> OTHER INFORMATION: siRNA

<400> SEQUENCE: 132
gaaatcccag tccacgcagt t                                      21

<210> SEQ ID NO 133

<400> SEQUENCE: 133

000

```
<210> SEQ ID NO 134
<211> LENGTH: 21
<212> TYPE: DNA
<213> ORGANISM: Artificial Sequence
<220> FEATURE:
<223> OTHER INFORMATION: siRNA

<400> SEQUENCE: 134
aatcccagtc cacgcagatt t                                                 21

<210> SEQ ID NO 135
<211> LENGTH: 21
<212> TYPE: DNA
<213> ORGANISM: Artificial Sequence
<220> FEATURE:
<223> OTHER INFORMATION: siRNA

<400> SEQUENCE: 135
atcccagtcc acgcagattt t                                                 21

<210> SEQ ID NO 136
<211> LENGTH: 21
<212> TYPE: DNA
<213> ORGANISM: Artificial Sequence
<220> FEATURE:
<223> OTHER INFORMATION: siRNA

<400> SEQUENCE: 136
tcccagtcca cgcagatttt t                                                 21

<210> SEQ ID NO 137
<211> LENGTH: 21
<212> TYPE: DNA
<213> ORGANISM: Artificial Sequence
<220> FEATURE:
<223> OTHER INFORMATION: siRNA

<400> SEQUENCE: 137
gtccacgcag atttcacagt t                                                 21

<210> SEQ ID NO 138
<211> LENGTH: 21
<212> TYPE: DNA
<213> ORGANISM: Artificial Sequence
<220> FEATURE:
<223> OTHER INFORMATION: siRNA

<400> SEQUENCE: 138
cgcagatttc acaggaactt t                                                 21

<210> SEQ ID NO 139
<211> LENGTH: 21
<212> TYPE: DNA
<213> ORGANISM: Artificial Sequence
<220> FEATURE:
<223> OTHER INFORMATION: siRNA

<400> SEQUENCE: 139
gatttcacag gaactggagt t                                                 21

<210> SEQ ID NO 140
<211> LENGTH: 21
<212> TYPE: DNA
<213> ORGANISM: Artificial Sequence
<220> FEATURE:
<223> OTHER INFORMATION: siRNA
```

```
<400> SEQUENCE: 140
tttcacagga actggaggat t                                              21

<210> SEQ ID NO 141
<211> LENGTH: 21
<212> TYPE: DNA
<213> ORGANISM: Artificial Sequence
<220> FEATURE:
<223> OTHER INFORMATION: siRNA

<400> SEQUENCE: 141
caggaactgg aggaacttct t                                              21

<210> SEQ ID NO 142
<211> LENGTH: 21
<212> TYPE: DNA
<213> ORGANISM: Artificial Sequence
<220> FEATURE:
<223> OTHER INFORMATION: siRNA

<400> SEQUENCE: 142
ggaactggag gaacttcgat t                                              21

<210> SEQ ID NO 143
<211> LENGTH: 21
<212> TYPE: DNA
<213> ORGANISM: Artificial Sequence
<220> FEATURE:
<223> OTHER INFORMATION: siRNA

<400> SEQUENCE: 143
actggaggaa cttcgagctt t                                              21

<210> SEQ ID NO 144
<211> LENGTH: 21
<212> TYPE: DNA
<213> ORGANISM: Artificial Sequence
<220> FEATURE:
<223> OTHER INFORMATION: siRNA

<400> SEQUENCE: 144
ctggaggaac ttcgagctgt t                                              21

<210> SEQ ID NO 145
<211> LENGTH: 21
<212> TYPE: DNA
<213> ORGANISM: Artificial Sequence
<220> FEATURE:
<223> OTHER INFORMATION: siRNA

<400> SEQUENCE: 145
ggaacttcga gctgaacagt t                                              21

<210> SEQ ID NO 146
<211> LENGTH: 21
<212> TYPE: DNA
<213> ORGANISM: Artificial Sequence
<220> FEATURE:
<223> OTHER INFORMATION: siRNA

<400> SEQUENCE: 146
acttcgagct gaacagcagt t                                              21

<210> SEQ ID NO 147
<211> LENGTH: 21
<212> TYPE: DNA
```

```
<213> ORGANISM: Artificial Sequence
<220> FEATURE:
<223> OTHER INFORMATION: siRNA

<400> SEQUENCE: 147
cttcgagctg aacagcagat t                                              21

<210> SEQ ID NO 148
<211> LENGTH: 21
<212> TYPE: DNA
<213> ORGANISM: Artificial Sequence
<220> FEATURE:
<223> OTHER INFORMATION: siRNA

<400> SEQUENCE: 148
acctgaacgg gcttcaagct t                                              21

<210> SEQ ID NO 149
<211> LENGTH: 21
<212> TYPE: DNA
<213> ORGANISM: Artificial Sequence
<220> FEATURE:
<223> OTHER INFORMATION: siRNA

<400> SEQUENCE: 149
cctgaacggg cttcaagcat t                                              21

<210> SEQ ID NO 150
<211> LENGTH: 21
<212> TYPE: DNA
<213> ORGANISM: Artificial Sequence
<220> FEATURE:
<223> OTHER INFORMATION: siRNA

<400> SEQUENCE: 150
acgggcttca agcagatctt t                                              21

<210> SEQ ID NO 151
<211> LENGTH: 21
<212> TYPE: DNA
<213> ORGANISM: Artificial Sequence
<220> FEATURE:
<223> OTHER INFORMATION: siRNA

<400> SEQUENCE: 151
cgggcttcaa gcagatctgt t                                              21

<210> SEQ ID NO 152
<211> LENGTH: 21
<212> TYPE: DNA
<213> ORGANISM: Artificial Sequence
<220> FEATURE:
<223> OTHER INFORMATION: siRNA

<400> SEQUENCE: 152
agcagatctg agcagcttct t                                              21

<210> SEQ ID NO 153
<211> LENGTH: 21
<212> TYPE: DNA
<213> ORGANISM: Artificial Sequence
<220> FEATURE:
<223> OTHER INFORMATION: siRNA

<400> SEQUENCE: 153
gcagatctga gcagcttcat t                                              21
```

<210> SEQ ID NO 154
<211> LENGTH: 21
<212> TYPE: DNA
<213> ORGANISM: Artificial Sequence
<220> FEATURE:
<223> OTHER INFORMATION: siRNA

<400> SEQUENCE: 154
gatctgagca gcttcaagtt t                                           21

<210> SEQ ID NO 155
<211> LENGTH: 21
<212> TYPE: DNA
<213> ORGANISM: Artificial Sequence
<220> FEATURE:
<223> OTHER INFORMATION: siRNA

<400> SEQUENCE: 155
tctgagcagc ttcaagtcct t                                           21

<210> SEQ ID NO 156
<211> LENGTH: 21
<212> TYPE: DNA
<213> ORGANISM: Artificial Sequence
<220> FEATURE:
<223> OTHER INFORMATION: siRNA

<400> SEQUENCE: 156
ctgagcagct tcaagtccct t                                           21

<210> SEQ ID NO 157
<211> LENGTH: 21
<212> TYPE: DNA
<213> ORGANISM: Artificial Sequence
<220> FEATURE:
<223> OTHER INFORMATION: siRNA

<400> SEQUENCE: 157
gcagcttcaa gtcccaggat t                                           21

<210> SEQ ID NO 158
<211> LENGTH: 21
<212> TYPE: DNA
<213> ORGANISM: Artificial Sequence
<220> FEATURE:
<223> OTHER INFORMATION: siRNA

<400> SEQUENCE: 158
gcttcaagtc ccaggaattt t                                           21

<210> SEQ ID NO 159
<211> LENGTH: 21
<212> TYPE: DNA
<213> ORGANISM: Artificial Sequence
<220> FEATURE:
<223> OTHER INFORMATION: siRNA

<400> SEQUENCE: 159
agtcccagga attgaacgat t                                           21

<210> SEQ ID NO 160
<211> LENGTH: 21
<212> TYPE: DNA
<213> ORGANISM: Artificial Sequence
<220> FEATURE:
<223> OTHER INFORMATION: siRNA

```
<400> SEQUENCE: 160
gtcccaggaa ttgaacgagt t                                              21

<210> SEQ ID NO 161
<211> LENGTH: 21
<212> TYPE: DNA
<213> ORGANISM: Artificial Sequence
<220> FEATURE:
<223> OTHER INFORMATION: siRNA

<400> SEQUENCE: 161
attgaacgag aggaacgaat t                                              21

<210> SEQ ID NO 162
<211> LENGTH: 21
<212> TYPE: DNA
<213> ORGANISM: Artificial Sequence
<220> FEATURE:
<223> OTHER INFORMATION: siRNA

<400> SEQUENCE: 162
ttgaacgaga ggaacgaagt t                                              21

<210> SEQ ID NO 163
<211> LENGTH: 21
<212> TYPE: DNA
<213> ORGANISM: Artificial Sequence
<220> FEATURE:
<223> OTHER INFORMATION: siRNA

<400> SEQUENCE: 163
acgagaggaa cgaagcttct t                                              21

<210> SEQ ID NO 164
<211> LENGTH: 21
<212> TYPE: DNA
<213> ORGANISM: Artificial Sequence
<220> FEATURE:
<223> OTHER INFORMATION: siRNA

<400> SEQUENCE: 164
cgagaggaac gaagcttcat t                                              21

<210> SEQ ID NO 165
<211> LENGTH: 21
<212> TYPE: DNA
<213> ORGANISM: Artificial Sequence
<220> FEATURE:
<223> OTHER INFORMATION: siRNA

<400> SEQUENCE: 165
tttgctggaa agactccggt t                                              21

<210> SEQ ID NO 166
<211> LENGTH: 21
<212> TYPE: DNA
<213> ORGANISM: Artificial Sequence
<220> FEATURE:
<223> OTHER INFORMATION: siRNA

<400> SEQUENCE: 166
aagactccgg gaggaggtgt t                                              21

<210> SEQ ID NO 167
<211> LENGTH: 21
<212> TYPE: DNA
```

```
<213> ORGANISM: Artificial Sequence
<220> FEATURE:
<223> OTHER INFORMATION: siRNA

<400> SEQUENCE: 167
agactccggg aggaggtgat t                                              21

<210> SEQ ID NO 168
<211> LENGTH: 21
<212> TYPE: DNA
<213> ORGANISM: Artificial Sequence
<220> FEATURE:
<223> OTHER INFORMATION: siRNA

<400> SEQUENCE: 168
gactccggga ggaggtgact t                                              21

<210> SEQ ID NO 169
<211> LENGTH: 21
<212> TYPE: DNA
<213> ORGANISM: Artificial Sequence
<220> FEATURE:
<223> OTHER INFORMATION: siRNA

<400> SEQUENCE: 169
ctccgggagg aggtgacaat t                                              21

<210> SEQ ID NO 170
<211> LENGTH: 21
<212> TYPE: DNA
<213> ORGANISM: Artificial Sequence
<220> FEATURE:
<223> OTHER INFORMATION: siRNA

<400> SEQUENCE: 170
ggaggtgaca aagctaaggt t                                              21

<210> SEQ ID NO 171
<211> LENGTH: 21
<212> TYPE: DNA
<213> ORGANISM: Artificial Sequence
<220> FEATURE:
<223> OTHER INFORMATION: siRNA

<400> SEQUENCE: 171
ggtgacaaag ctaaggatgt t                                              21

<210> SEQ ID NO 172
<211> LENGTH: 21
<212> TYPE: DNA
<213> ORGANISM: Artificial Sequence
<220> FEATURE:
<223> OTHER INFORMATION: siRNA

<400> SEQUENCE: 172
caaagctaag gatggagttt t                                              21

<210> SEQ ID NO 173
<211> LENGTH: 21
<212> TYPE: DNA
<213> ORGANISM: Artificial Sequence
<220> FEATURE:
<223> OTHER INFORMATION: siRNA

<400> SEQUENCE: 173
aagctaagga tggagttgct t                                              21
```

<210> SEQ ID NO 174
<211> LENGTH: 21
<212> TYPE: DNA
<213> ORGANISM: Artificial Sequence
<220> FEATURE:
<223> OTHER INFORMATION: siRNA

<400> SEQUENCE: 174
agctaaggat ggagttgcat t                                             21

<210> SEQ ID NO 175
<211> LENGTH: 21
<212> TYPE: DNA
<213> ORGANISM: Artificial Sequence
<220> FEATURE:
<223> OTHER INFORMATION: siRNA

<400> SEQUENCE: 175
gctaaggatg gagttgcagt t                                             21

<210> SEQ ID NO 176
<211> LENGTH: 21
<212> TYPE: DNA
<213> ORGANISM: Artificial Sequence
<220> FEATURE:
<223> OTHER INFORMATION: siRNA

<400> SEQUENCE: 176
aggatggagt tgcaggtgtt t                                             21

<210> SEQ ID NO 177
<211> LENGTH: 21
<212> TYPE: DNA
<213> ORGANISM: Artificial Sequence
<220> FEATURE:
<223> OTHER INFORMATION: siRNA

<400> SEQUENCE: 177
ggatggagtt gcaggtgtct t                                             21

<210> SEQ ID NO 178
<211> LENGTH: 21
<212> TYPE: DNA
<213> ORGANISM: Artificial Sequence
<220> FEATURE:
<223> OTHER INFORMATION: siRNA

<400> SEQUENCE: 178
tggagttgca ggtgtccagt t                                             21

<210> SEQ ID NO 179
<211> LENGTH: 21
<212> TYPE: DNA
<213> ORGANISM: Artificial Sequence
<220> FEATURE:
<223> OTHER INFORMATION: siRNA

<400> SEQUENCE: 179
gttgcaggtg tccagcggct t                                             21

<210> SEQ ID NO 180
<211> LENGTH: 21
<212> TYPE: DNA
<213> ORGANISM: Artificial Sequence
<220> FEATURE:
<223> OTHER INFORMATION: siRNA

```
<400> SEQUENCE: 180
ggtgtccagc ggctttgtgt t                                              21

<210> SEQ ID NO 181
<211> LENGTH: 21
<212> TYPE: DNA
<213> ORGANISM: Artificial Sequence
<220> FEATURE:
<223> OTHER INFORMATION: siRNA

<400> SEQUENCE: 181
gcggctttgt gtgcaacact t                                              21

<210> SEQ ID NO 182
<211> LENGTH: 21
<212> TYPE: DNA
<213> ORGANISM: Artificial Sequence
<220> FEATURE:
<223> OTHER INFORMATION: siRNA

<400> SEQUENCE: 182
acacgtgccc tgaaaagtgt t                                              21

<210> SEQ ID NO 183
<211> LENGTH: 21
<212> TYPE: DNA
<213> ORGANISM: Artificial Sequence
<220> FEATURE:
<223> OTHER INFORMATION: siRNA

<400> SEQUENCE: 183
cacgtgccct gaaaagtggt t                                              21

<210> SEQ ID NO 184
<211> LENGTH: 21
<212> TYPE: DNA
<213> ORGANISM: Artificial Sequence
<220> FEATURE:
<223> OTHER INFORMATION: siRNA

<400> SEQUENCE: 184
cgtgccctga aaagtggatt t                                              21

<210> SEQ ID NO 185
<211> LENGTH: 21
<212> TYPE: DNA
<213> ORGANISM: Artificial Sequence
<220> FEATURE:
<223> OTHER INFORMATION: siRNA

<400> SEQUENCE: 185
aaagtggatc aatttccaat t                                              21

<210> SEQ ID NO 186
<211> LENGTH: 21
<212> TYPE: DNA
<213> ORGANISM: Artificial Sequence
<220> FEATURE:
<223> OTHER INFORMATION: siRNA

<400> SEQUENCE: 186
aagtggatca atttccaact t                                              21

<210> SEQ ID NO 187
<211> LENGTH: 21
<212> TYPE: DNA
```

```
<213> ORGANISM: Artificial Sequence
<220> FEATURE:
<223> OTHER INFORMATION: siRNA

<400> SEQUENCE: 187
agtggatcaa tttccaacgt t                                              21

<210> SEQ ID NO 188
<211> LENGTH: 21
<212> TYPE: DNA
<213> ORGANISM: Artificial Sequence
<220> FEATURE:
<223> OTHER INFORMATION: siRNA

<400> SEQUENCE: 188
gtggatcaat ttccaacggt t                                              21

<210> SEQ ID NO 189
<211> LENGTH: 21
<212> TYPE: DNA
<213> ORGANISM: Artificial Sequence
<220> FEATURE:
<223> OTHER INFORMATION: siRNA

<400> SEQUENCE: 189
tcaatttcca acggaagtgt t                                              21

<210> SEQ ID NO 190
<211> LENGTH: 21
<212> TYPE: DNA
<213> ORGANISM: Artificial Sequence
<220> FEATURE:
<223> OTHER INFORMATION: siRNA

<400> SEQUENCE: 190
atttccaacg gaagtgctat t                                              21

<210> SEQ ID NO 191
<211> LENGTH: 21
<212> TYPE: DNA
<213> ORGANISM: Artificial Sequence
<220> FEATURE:
<223> OTHER INFORMATION: siRNA

<400> SEQUENCE: 191
tttccaacgg aagtgctact t                                              21

<210> SEQ ID NO 192
<211> LENGTH: 21
<212> TYPE: DNA
<213> ORGANISM: Artificial Sequence
<220> FEATURE:
<223> OTHER INFORMATION: siRNA

<400> SEQUENCE: 192
acggaagtgc tactacttct t                                              21

<210> SEQ ID NO 193
<211> LENGTH: 21
<212> TYPE: DNA
<213> ORGANISM: Artificial Sequence
<220> FEATURE:
<223> OTHER INFORMATION: siRNA

<400> SEQUENCE: 193
cggaagtgct actacttcgt t                                              21
```

```
<210> SEQ ID NO 194
<211> LENGTH: 21
<212> TYPE: DNA
<213> ORGANISM: Artificial Sequence
<220> FEATURE:
<223> OTHER INFORMATION: siRNA

<400> SEQUENCE: 194
agtgctacta cttcggcaat t                                              21

<210> SEQ ID NO 195
<211> LENGTH: 21
<212> TYPE: DNA
<213> ORGANISM: Artificial Sequence
<220> FEATURE:
<223> OTHER INFORMATION: siRNA

<400> SEQUENCE: 195
gtgctactac ttcggcaagt t                                              21

<210> SEQ ID NO 196
<211> LENGTH: 21
<212> TYPE: DNA
<213> ORGANISM: Artificial Sequence
<220> FEATURE:
<223> OTHER INFORMATION: siRNA

<400> SEQUENCE: 196
ctacttcggc aagggcacct t                                              21

<210> SEQ ID NO 197
<211> LENGTH: 21
<212> TYPE: DNA
<213> ORGANISM: Artificial Sequence
<220> FEATURE:
<223> OTHER INFORMATION: siRNA

<400> SEQUENCE: 197
cttcggcaag ggcaccaagt t                                              21

<210> SEQ ID NO 198
<211> LENGTH: 21
<212> TYPE: DNA
<213> ORGANISM: Artificial Sequence
<220> FEATURE:
<223> OTHER INFORMATION: siRNA

<400> SEQUENCE: 198
agggcaccaa gcagtgggtt t                                              21

<210> SEQ ID NO 199
<211> LENGTH: 21
<212> TYPE: DNA
<213> ORGANISM: Artificial Sequence
<220> FEATURE:
<223> OTHER INFORMATION: siRNA

<400> SEQUENCE: 199
gggcaccaag cagtgggtct t                                              21

<210> SEQ ID NO 200
<211> LENGTH: 21
<212> TYPE: DNA
<213> ORGANISM: Artificial Sequence
<220> FEATURE:
<223> OTHER INFORMATION: siRNA
```

```
<400> SEQUENCE: 200
cgcccggtat gcctgtgact t                                              21

<210> SEQ ID NO 201
<211> LENGTH: 21
<212> TYPE: DNA
<213> ORGANISM: Artificial Sequence
<220> FEATURE:
<223> OTHER INFORMATION: siRNA

<400> SEQUENCE: 201
tgcctgtgac gacatggaat t                                              21

<210> SEQ ID NO 202
<211> LENGTH: 21
<212> TYPE: DNA
<213> ORGANISM: Artificial Sequence
<220> FEATURE:
<223> OTHER INFORMATION: siRNA

<400> SEQUENCE: 202
cgacatggaa gggcagctgt t                                              21

<210> SEQ ID NO 203
<211> LENGTH: 21
<212> TYPE: DNA
<213> ORGANISM: Artificial Sequence
<220> FEATURE:
<223> OTHER INFORMATION: siRNA

<400> SEQUENCE: 203
catggaaggg cagctggtct t                                              21

<210> SEQ ID NO 204
<211> LENGTH: 21
<212> TYPE: DNA
<213> ORGANISM: Artificial Sequence
<220> FEATURE:
<223> OTHER INFORMATION: siRNA

<400> SEQUENCE: 204
tggaagggca gctggtcagt t                                              21

<210> SEQ ID NO 205
<211> LENGTH: 21
<212> TYPE: DNA
<213> ORGANISM: Artificial Sequence
<220> FEATURE:
<223> OTHER INFORMATION: siRNA

<400> SEQUENCE: 205
agggcagctg gtcagcatct t                                              21

<210> SEQ ID NO 206
<211> LENGTH: 21
<212> TYPE: DNA
<213> ORGANISM: Artificial Sequence
<220> FEATURE:
<223> OTHER INFORMATION: siRNA

<400> SEQUENCE: 206
gggcagctgg tcagcatcct t                                              21

<210> SEQ ID NO 207
<211> LENGTH: 21
<212> TYPE: DNA
```

<213> ORGANISM: Artificial Sequence
<220> FEATURE:
<223> OTHER INFORMATION: siRNA

<400> SEQUENCE: 207
agctggtcag catccacagt t                                             21

<210> SEQ ID NO 208
<211> LENGTH: 21
<212> TYPE: DNA
<213> ORGANISM: Artificial Sequence
<220> FEATURE:
<223> OTHER INFORMATION: siRNA

<400> SEQUENCE: 208
gctggtcagc atccacagct t                                             21

<210> SEQ ID NO 209
<211> LENGTH: 21
<212> TYPE: DNA
<213> ORGANISM: Artificial Sequence
<220> FEATURE:
<223> OTHER INFORMATION: siRNA

<400> SEQUENCE: 209
cagcccggag gagcaggact t                                             21

<210> SEQ ID NO 210
<211> LENGTH: 21
<212> TYPE: DNA
<213> ORGANISM: Artificial Sequence
<220> FEATURE:
<223> OTHER INFORMATION: siRNA

<400> SEQUENCE: 210
ggagcaggac ttcctgacct t                                             21

<210> SEQ ID NO 211
<211> LENGTH: 21
<212> TYPE: DNA
<213> ORGANISM: Artificial Sequence
<220> FEATURE:
<223> OTHER INFORMATION: siRNA

<400> SEQUENCE: 211
gcaggacttc ctgaccaagt t                                             21

<210> SEQ ID NO 212
<211> LENGTH: 21
<212> TYPE: DNA
<213> ORGANISM: Artificial Sequence
<220> FEATURE:
<223> OTHER INFORMATION: siRNA

<400> SEQUENCE: 212
ggacttcctg accaagcatt t                                             21

<210> SEQ ID NO 213
<211> LENGTH: 21
<212> TYPE: DNA
<213> ORGANISM: Artificial Sequence
<220> FEATURE:
<223> OTHER INFORMATION: siRNA

<400> SEQUENCE: 213
cttcctgacc aagcatgcct t                                             21

<210> SEQ ID NO 214
<211> LENGTH: 21
<212> TYPE: DNA
<213> ORGANISM: Artificial Sequence
<220> FEATURE:
<223> OTHER INFORMATION: siRNA

<400> SEQUENCE: 214
ccaagcatgc cagccacact t                                              21

<210> SEQ ID NO 215
<211> LENGTH: 21
<212> TYPE: DNA
<213> ORGANISM: Artificial Sequence
<220> FEATURE:
<223> OTHER INFORMATION: siRNA

<400> SEQUENCE: 215
agcatgccag ccacaccggt t                                              21

<210> SEQ ID NO 216
<211> LENGTH: 21
<212> TYPE: DNA
<213> ORGANISM: Artificial Sequence
<220> FEATURE:
<223> OTHER INFORMATION: siRNA

<400> SEQUENCE: 216
gccacaccgg ctcctggatt t                                              21

<210> SEQ ID NO 217
<211> LENGTH: 21
<212> TYPE: DNA
<213> ORGANISM: Artificial Sequence
<220> FEATURE:
<223> OTHER INFORMATION: siRNA

<400> SEQUENCE: 217
caccggctcc tggattggct t                                              21

<210> SEQ ID NO 218
<211> LENGTH: 21
<212> TYPE: DNA
<213> ORGANISM: Artificial Sequence
<220> FEATURE:
<223> OTHER INFORMATION: siRNA

<400> SEQUENCE: 218
ccggctcctg gattggcctt t                                              21

<210> SEQ ID NO 219
<211> LENGTH: 21
<212> TYPE: DNA
<213> ORGANISM: Artificial Sequence
<220> FEATURE:
<223> OTHER INFORMATION: siRNA

<400> SEQUENCE: 219
ttggccttcg gaacttggat t                                              21

<210> SEQ ID NO 220
<211> LENGTH: 21
<212> TYPE: DNA
<213> ORGANISM: Artificial Sequence
<220> FEATURE:
<223> OTHER INFORMATION: siRNA

```
<400> SEQUENCE: 220
acttggacct gaagggggat t                                      21

<210> SEQ ID NO 221
<211> LENGTH: 21
<212> TYPE: DNA
<213> ORGANISM: Artificial Sequence
<220> FEATURE:
<223> OTHER INFORMATION: siRNA

<400> SEQUENCE: 221
cttggacctg aaggggagt t                                       21

<210> SEQ ID NO 222
<211> LENGTH: 21
<212> TYPE: DNA
<213> ORGANISM: Artificial Sequence
<220> FEATURE:
<223> OTHER INFORMATION: siRNA

<400> SEQUENCE: 222
cctgaagggg gagtttatct t                                      21

<210> SEQ ID NO 223
<211> LENGTH: 21
<212> TYPE: DNA
<213> ORGANISM: Artificial Sequence
<220> FEATURE:
<223> OTHER INFORMATION: siRNA

<400> SEQUENCE: 223 aggggagtt tatctgggtt t                                       21

<210> SEQ ID NO 224
<211> LENGTH: 21
<212> TYPE: DNA
<213> ORGANISM: Artificial Sequence
<220> FEATURE:
<223> OTHER INFORMATION: siRNA

<400> SEQUENCE: 224
gggggagttt atctgggtgt t                                      21

<210> SEQ ID NO 225
<211> LENGTH: 21
<212> TYPE: DNA
<213> ORGANISM: Artificial Sequence
<220> FEATURE:
<223> OTHER INFORMATION: siRNA

<400> SEQUENCE: 225
gtttatctgg gtggatgggt t                                      21

<210> SEQ ID NO 226
<211> LENGTH: 21
<212> TYPE: DNA
<213> ORGANISM: Artificial Sequence
<220> FEATURE:
<223> OTHER INFORMATION: siRNA

<400> SEQUENCE: 226
tctgggtgga tgggagccat t                                      21

<210> SEQ ID NO 227
<211> LENGTH: 21
<212> TYPE: DNA
```

```
<213> ORGANISM: Artificial Sequence
<220> FEATURE:
<223> OTHER INFORMATION: siRNA

<400> SEQUENCE: 227
tgggagccac gtggactact t                                              21

<210> SEQ ID NO 228
<211> LENGTH: 21
<212> TYPE: DNA
<213> ORGANISM: Artificial Sequence
<220> FEATURE:
<223> OTHER INFORMATION: siRNA

<400> SEQUENCE: 228
gccacgtgga ctacagcaat t                                              21

<210> SEQ ID NO 229
<211> LENGTH: 21
<212> TYPE: DNA
<213> ORGANISM: Artificial Sequence
<220> FEATURE:
<223> OTHER INFORMATION: siRNA

<400> SEQUENCE: 229
cgtggactac agcaactggt t                                              21

<210> SEQ ID NO 230
<211> LENGTH: 21
<212> TYPE: DNA
<213> ORGANISM: Artificial Sequence
<220> FEATURE:
<223> OTHER INFORMATION: siRNA

<400> SEQUENCE: 230
ctacagcaac tgggctccat t                                              21

<210> SEQ ID NO 231
<211> LENGTH: 21
<212> TYPE: DNA
<213> ORGANISM: Artificial Sequence
<220> FEATURE:
<223> OTHER INFORMATION: siRNA

<400> SEQUENCE: 231
cagcaactgg gctccagggt t                                              21

<210> SEQ ID NO 232
<211> LENGTH: 21
<212> TYPE: DNA
<213> ORGANISM: Artificial Sequence
<220> FEATURE:
<223> OTHER INFORMATION: siRNA

<400> SEQUENCE: 232
gggcgaggac tgcgtgatgt t                                              21

<210> SEQ ID NO 233

<400> SEQUENCE: 233

000

<210> SEQ ID NO 234
<211> LENGTH: 21
<212> TYPE: DNA
<213> ORGANISM: Artificial Sequence
```

<220> FEATURE:
<223> OTHER INFORMATION: siRNA

<400> SEQUENCE: 234
ggactgcgtg atgatgcggt t                                              21

<210> SEQ ID NO 235
<211> LENGTH: 21
<212> TYPE: DNA
<213> ORGANISM: Artificial Sequence
<220> FEATURE:
<223> OTHER INFORMATION: siRNA

<400> SEQUENCE: 235
ctgcgtgatg atgcggggct t                                              21

<210> SEQ ID NO 236
<211> LENGTH: 21
<212> TYPE: DNA
<213> ORGANISM: Artificial Sequence
<220> FEATURE:
<223> OTHER INFORMATION: siRNA

<400> SEQUENCE: 236
acgacgcctt ctgcgaccgt t                                              21

<210> SEQ ID NO 237
<211> LENGTH: 21
<212> TYPE: DNA
<213> ORGANISM: Artificial Sequence
<220> FEATURE:
<223> OTHER INFORMATION: siRNA

<400> SEQUENCE: 237
cgacgccttc tgcgaccgtt t                                              21

<210> SEQ ID NO 238
<211> LENGTH: 21
<212> TYPE: DNA
<213> ORGANISM: Artificial Sequence
<220> FEATURE:
<223> OTHER INFORMATION: siRNA

<400> SEQUENCE: 238
cgccttctgc gaccgtaagt t                                              21

<210> SEQ ID NO 239
<211> LENGTH: 21
<212> TYPE: DNA
<213> ORGANISM: Artificial Sequence
<220> FEATURE:
<223> OTHER INFORMATION: siRNA

<400> SEQUENCE: 239
gcgaaggttc cgcggagtct t                                              21

<210> SEQ ID NO 240
<211> LENGTH: 21
<212> TYPE: DNA
<213> ORGANISM: Artificial Sequence
<220> FEATURE:
<223> OTHER INFORMATION: siRNA

<400> SEQUENCE: 240
aggttccgcg gagtccatgt t                                              21

```
<210> SEQ ID NO 241
<211> LENGTH: 21
<212> TYPE: DNA
<213> ORGANISM: Artificial Sequence
<220> FEATURE:
<223> OTHER INFORMATION: siRNA

<400> SEQUENCE: 241
ggttccgcgg agtccatggt t                                             21

<210> SEQ ID NO 242
<211> LENGTH: 21
<212> TYPE: DNA
<213> ORGANISM: Artificial Sequence
<220> FEATURE:
<223> OTHER INFORMATION: siRNA

<400> SEQUENCE: 242
gtccatggga cctgattcat t                                             21

<210> SEQ ID NO 243
<211> LENGTH: 21
<212> TYPE: DNA
<213> ORGANISM: Artificial Sequence
<220> FEATURE:
<223> OTHER INFORMATION: siRNA

<400> SEQUENCE: 243
tgggacctga ttcaagacct t                                             21

<210> SEQ ID NO 244
<211> LENGTH: 21
<212> TYPE: DNA
<213> ORGANISM: Artificial Sequence
<220> FEATURE:
<223> OTHER INFORMATION: siRNA

<400> SEQUENCE: 244
cctgattcaa gaccagacct t                                             21

<210> SEQ ID NO 245
<211> LENGTH: 21
<212> TYPE: DNA
<213> ORGANISM: Artificial Sequence
<220> FEATURE:
<223> OTHER INFORMATION: siRNA

<400> SEQUENCE: 245
ttcaagacca gaccctgact t                                             21

<210> SEQ ID NO 246
<211> LENGTH: 21
<212> TYPE: DNA
<213> ORGANISM: Artificial Sequence
<220> FEATURE:
<223> OTHER INFORMATION: siRNA

<400> SEQUENCE: 246
ccctctgccc ctctccactt t                                             21

<210> SEQ ID NO 247
<211> LENGTH: 21
<212> TYPE: DNA
<213> ORGANISM: Artificial Sequence
```

```
-continued

<220> FEATURE:
<223> OTHER INFORMATION: siRNA

<400> SEQUENCE: 247
ctcttgagca tggatacagt t                                          21
```

COMPOSITIONS AND METHODS TO TREAT ASTHMA

This application is a continuation-in-part of PCT/US09/34300 filed Feb. 17, 2009 which in turn claims priority under 35 U.S.C. §119(e) to U.S. Provisional Patent Application 61/028,699, filed on Feb. 14, 2008. Each of the aforementioned applications is incorporated by reference herein.

Pursuant to 35 U.S.C. §202(c), it is acknowledged that the United States Government has rights in the invention described herein, which was made in part with funds from the National Institutes of Health Grant Nos. HL-31467 and HL-61038.

FIELD OF THE INVENTION

The present invention relates to the fields of medicine, molecular biology and therapeutic treatment of disease. More specifically, the invention provides CD23 siRNA compositions and methods of use thereof for the treatment of asthma.

BACKGROUND OF THE INVENTION

Several publications and patent documents are cited throughout the specification in order to describe the state of the art to which this invention pertains. Each of these citations is incorporated herein by reference as though set forth in full.

The present invention relates to asthma therapy. Bronchial asthma in mammals is characterized by inflammation of the airways, exaggerated airway reactivity to bronchoconstrictor agonists, and attenuated beta-adrenoceptor-mediated airway relaxation (Bai, 1990 Am. Rev. Respir. Dis. 141:552-557; Goldie et al., 1986, Br. J. Clin. Pharmacol. 22:669-676; McFadden et al., 1994, Am. J. Respir. Crit. Care Med. 150: 523-526). In humans with atopic asthma, mast cell activation has been implicated in mediating the immediate bronchoconstrictor response which acutely follows antigen inhalation. This response is a process which involves IgE-mediated activation of the high affinity IgE receptor (FcεRI), leading to cellular degranulation and the release of various mast cell-derived mediators including histamine, eicosanoids, and specific cytokines (Metzger, 1992, Immunol. Rev. 125:37-48; Beaven et al., 1993, Immunol. Today 14:222-226; Galli, 1993, N. Engl. J. Meda 328:257-265).

The identification of Fc receptors on other cell types in the lung (e.g., mononuclear cells, eosinophils, and dendritic cells) suggests that, apart from mast cells per se, these other cell types may also serve to propagate the pro-inflammatory allergic pulmonary response, most likely via the orchestrated extended release of various cytokines (Walker et al., 1992, Am. Rev. Respir. Dis. 146:109-115; Watson et al., 1993, Am. J. Respir. Cell Mol. Biol. 8:365-369; Capron et al., 1984, J. Immunol. 132:462-468; Beasley et al., 1989, Am. Rev. Respir. Dis. 139:806-817; Litchfield et al., 1992, J. Asthma 29:181-191; Barnes et al., 1988, Pharmacol. Rev. 40:49-84; Borish et al., 1991, J. Immunol. 146:63-67). It is believed that immune complex/Fc receptor interactions expressed by these cells, i.e., mononuclear cells, eosinophils, and dendritic cells, potentially underlie the progression of the airway inflammatory and bronchoconstrictor responses in asthma, wherein the immediate bronchoconstriction accompanying antigen exposure is followed by the development of the late phase asthmatic response involving various proinflammatory cells. Indeed, recent studies have demonstrated that expression of the inducible form of the low affinity IgE receptor (FcεRII or CD23) is upregulated on monocytes and alveolar macrophages (Williams et al., 1992, J. Immunol. 149:2823-2829), as well as on circulating B lymphocytes (Gagro et al., 1993, Int. Arch. Allergy Immunol. 101:203-208; Rabatic et al., 1993, Exp. Immunol. 94:337-340) isolated from atopic asthmatic subjects. Similarly, exposure of asthmatic subjects to allergen and treatment of isolated monocytes with specific cytokines have been shown to up-regulate FcεRII expression on mononuclear phagocytes (Williams et al., 1992, J. Immunol. 149: 2823-2829; Joseph et al., 1983, J. Clin. Invest. 71:221-230). These findings suggest that altered Fc receptor expression and action in some cell types may contribute to the overall pro-inflammatory asthmatic response. While it is known that exposure of isolated rabbit and human airway smooth muscle (ASM) to atopic asthmatic serum induces the autocrine release and action of specific cytokines (notably Interleukins) by the sensitized ASM cells (Hakonarson et al., 1997, J. Clin. Invest. 99:117-124), the mechanism by which this sensitization is mediated has not been disclosed.

Current treatment options for asthma include medications that control the airway inflammatory component of the disease, (e.g., primarily corticosteroids, sodium cromolyn, methylxanthines, leukotriene modifiers), systemic administration of an anti-IgE antibody (e.g., Xolair), and rapid relief medications that counteract bronchospasm, (e.g., primarily beta-adrenergic agents). There are several disadvantages to using these medications as follows. There is a potential lack of effective sustained action; there are side effects associated with prolonged use of these medications, particularly in the case of corticosteroids and beta-adrenergic agents; there is a progressive loss of sensitivity to these treatments after prolonged use; there is limited efficacy of any of these agents in severe cases of asthma; these agents are non-selective, i.e., they do not specifically target the lung, therefore, side-effects affecting other organs are a potential risk. Furthermore, there are data which document an increased risk of dying from bronchial asthma following prolonged treatment of asthma using long-acting beta-adrenergic agents such as fenoterol (Pearce et al., 1990, Thorax 45:170-175; Spitzer et al., 1992, N. Engl. J. Med. 326:560-561).

Approximately fifteen million individuals in the U.S. have asthma and the disease is the cause of more than five thousand deaths annually in the U.S. In children, asthma represents the most prevalent chronic disease, requiring the most frequent use of emergency room visits and hospitalizations. The overall annual cost for asthma care in the U.S. is estimated to be in the range of billions of dollars. Although the disease represents a complex genetic disorder wherein multiple genes interact with each other and with the environment to trigger variable expression of the asthma phenotype, it is well established that IgE plays a central role in mediating the pulmonary inflammatory response and associated altered airway reactivity seen in allergic asthmatic individuals.

It has previously been shown that (1) airway smooth muscle (ASM) cells express CD23, the low affinity receptor for IgE, (2) CD23 expression is increased in ASM tissues isolated from allergic asthmatic individuals, and (3) activation of CD23 in ASM tissues by exposure to either high IgE-containing serum from atopic asthmatic individuals or IgE immune complexes elicits pro-asthmatic changes in ASM constrictor and relaxation responsiveness that characterize allergic asthma.

Accordingly, there exists a need for other safe and effective novel compositions and methods for treatment of asthma. The present invention satisfies this need and provides related advantages that overcome some of the deficiencies of the prior art.

SUMMARY OF THE INVENTION

In accordance with the present invention, a composition of matter comprising CD23 siRNA is provided. In a particularly preferred embodiment, the CD23 siRNA is contained in an aerosolized formulation.

In one aspect of the invention a siRNA composition comprising at least one nucleotide sequence selected from the group consisting of SEQ ID NO: 3 through SEQ ID NO: 10 is provided.

Also disclosed is a method of inhibiting the expression of CD23 in a patient comprising, administering siRNA molecules that direct cleavage of a target CD23 mRNA sequence to the pulmonary system of said patient. The method may also entail administration of one or more conventionally used anti-inflammatory or anti-asthmatic agents.

BRIEF DESCRIPTION OF THE DRAWINGS

FIG. 1. Efficiency assessment of human ASM cell transfection with a control fluorescin Cy™3-labeled siRNA duplex. Relative to direct administration of the Cy™3-labeled siRNA duplex (middle panels), incorporation of the siRNA duplex into ASM cell nuclei is markedly enhanced when using Oligofectamine as the transfection agent (upper panels). Cells exposed to non-labeled Oligofectamine alone show no evidence of non-specific fluorescence staining (lower panels).

FIG. 2. Inhibition of CD23a mRNA expression in ASM cells following Oligofectamine-mediated transfection with CD23 siRNAs. ASM cells constitutively express CD23a mRNA under control conditions. In contrast to the siRNA duplexes, #111062 (SEQ ID NOs: 3 and 4) and #106644 (SEQ ID NOs: 9 and 10), which have no effect, CD23 mRNA expression is distinctly inhibited in ASM cells that are transfected with either the #106645 (SEQ ID NO: 5 and 6) or #111060 (SEQ ID NO: 7 and 8) siRNA duplex, or a pool containing all of the siRNA preparations. α-actin was used as a control.

FIG. 3. siRNA inhibition of CD23a mRNA expression in vehicle-exposed and IL-13-treated ASM. Relative to vehicle-exposed cells, CD23a mRNA is increased in IL-13-treated ASM cells transfected with non-targeted (scrambled) siRNA. In contrast to the siRNA duplexes, #111062 (SEQ ID NOs: 3 and 4) and #106644 (SEQ ID NOs: 9 and 10), which have no effect, CD23 mRNA expression is markedly inhibited in both vehicle-exposed and IL-13-treated ASM cells that are transfected with either the #106645 (SEQ ID NO: 5 and 6) or #111060 (SEQ ID NO: 7 and 8) siRNA duplex, or a pool containing all of the siRNA preparations.

FIG. 4. CD23 siRNA inhibits pro-asthmatic changes in ASM tissue responsiveness. Relative to control serum-exposed rabbit ASM tissues, (A) constrictor responsiveness to ACh is increased and (B) relaxation responsiveness to isoproterenol is decreased in asthmatic (AS) serum-sensitized ASM tissues that are pre-treated with the scrambled (non-targeted) siRNA duplex. The pro-asthmatic changes in constrictor and relaxation responsiveness are ablated in AS serum-exposed ASM tissues that are pre-treated with the pool of siRNA duplexes targeted against CD23. Data represent mean±SE values.

FIG. 5. Comparison of constrictor responses to ACh (A) and relaxation responses to isoproterenol(B) in isolated rabbit ASM tissues exposed for 24 hr to IgE immune complexes in the absence and presence of the PDE4 inhibitor, rolipram.

FIG. 6. Top: Time-dependent increases in PDE4D mRNA transcripts detected by RT-PCR in cultured human ASM cells following exposure to IgE immune complexes. Bottom: Corresponding densitometric analysis of changes in PDE4D transcript levels, expressed as ratios of PDE4D-to-β-actin signals. Data are mean±SE values. $*p<0.05$; $**p<0.01$.

FIG. 7. Comparison of cAMP PDE activity in isolated rabbit ASM tissues exposed for 24 hr to vehicle alone (Control) and either allergic asthmatic (AS) serum (A) or IgE immune complexes (B) in the absence and presence of pretreatment with CD23 siRNA or rolipram.

FIG. 8. CD23 sequences. Both the nucleic acid (SEQ ID NO:1) and protein (SEQ ID NO: 2) sequences of CD23 from GenBank Accession number NM_002002 are shown.

DETAILED DESCRIPTION OF THE INVENTION

The invention relates to the discovery disclosed in U.S. Pat. No. 6,630,140 which demonstrated the presence of Fc receptors in ASM tissue and cultured ASM cells, and that specific activation of CD23 (i.e. FcϵRII) in rabbit ASM is associated with the induction of pro-asthmatic changes in agonist-mediated ASM constrictor and relaxant responsiveness. While expression of the receptor of the invention on other cell types is known, expression of the receptor on airway smooth muscle cells was previously unknown.

As it is presently understood, RNAi involves a multi-step process. Double stranded RNAs are cleaved by the endonuclease Dicer to generate nucleotide fragments (siRNA). The siRNA duplex is resolved into 2 single stranded RNAs, one strand being incorporated into a protein-containing complex where it functions as guide RNA to direct cleavage of the target RNA (Schwarz et al, Mol. Cell. 10:537 548 (2002), Zamore et al, Cell 101:25 33 (2000)), thus silencing a specific genetic message (see also Zeng et al, Proc. Natl. Acad. Sci. 100:9779 (2003)).

The invention includes a method of treating asthma in a mammal. An exemplary method entails administering to the mammal a pharmaceutically effective amount of CD23 siRNA. The siRNA inhibits the expression of the CD23 receptor protein, thereby inhibiting binding of IgE to CD23. Inhibition of binding of IgE to the CD23 receptor protein serves to diminish or ablate the asthmatic state in the mammal thereby treating asthma in the mammal. Preferably, the mammal is a human.

While Fcγ receptor subtype expression is present and similar in both isolated control and inherently atopic asthmatic ASM, expression of the low-affinity receptor for IgE (CD23/FcϵRII) is relatively markedly upregulated in the asthmatic tissue. There are also two types of FcϵRII receptor proteins, CD23a/FcϵRIIa and CD23b/FcϵRIIb, which differ in only six to seven N-terminal amino acids. Both receptor proteins are derived from the same gene through the use of different promoters which control expression of separate first exons of the protein, which exons are spliced to a common mRNA sequence (Delespease et al., 1992, Immunol. Rev. 125:78-97). The invention should be construed to include both receptor proteins.

Based on the foregoing observations, specific siRNA preparations directed at inhibiting the expression of CD23, the low-affinity receptor for IgE, as well as delivery methods are provided as a novel therapy to treat asthma. SiRNA oligonucleotides directed to CD23 specifically hybridize with nucleic acids encoding CD23 and interfere with CD23 gene expression. Inhibition of CD23 expression diminishes the altered constrictor and relaxation responsiveness in airway smooth muscle observed in the asthmatic patient. The compositions of the invention are preferably directly delivered to the lung. The siRNA can be delivered to a patient in vivo either systemically or locally with carriers, as discussed below.

Thus, a new approach for treating asthma is described herein. The compositions of the invention may be used alone or in combination with other anti-asthmatic agents or genes encoding anti-asthmatic proteins to augment the efficacy of the compositions.

To date, no CD23 antagonists that can be effectively used as inhaled agents have been identified. The present invention demonstrates that: (1) siRNA duplexes can be efficiently delivered into ASM cells using Oligofectamine as the transfection reagent; (2) transfection of human ASM cells with specific siRNA duplexes directed against CD23 effectively inhibit CD23 mRNA expression; and (3) pretreatment with these CD23 siRNA duplexes prevents the induction of asthma-like changes in ASM constrictor and relaxation responsiveness. Thus, delivery of these specific siRNA preparations directed against CD23 into the airways represents a novel approach to treat allergic asthma.

The following description sets forth the general procedures involved in practicing the present invention. To the extent that specific materials are mentioned, it is merely for purposes of illustration and is not intended to limit the invention. Unless otherwise specified, general biochemical and molecular biological procedures, such as those set forth in Sambrook et al., *Molecular Cloning*, Cold Spring Harbor Laboratory (1989) or Ausubel et al. (eds.) *Current Protocols in Molecular Biology*, John Wiley & Sons (1997) are used.

I. Definitions:

The following definitions are provided to facilitate an understanding of the present invention:

By the term "asthmatic state" as used herein, is meant the pro-asthmatic phenotype which is observed in airway smooth muscle cells. This phenotype is characterized by increased contraction and decreased relaxation of the airway tissue when it has been exposed for extended time periods to cAMP-elevating agents such as beta2-adrenergic agonists, pro-asthmatic stimuli such as specific cytokines, high IgE-containing atopic asthmatic serum or exogenous IgE, compared with airway tissue which has not been exposed to these agents or stimuli. By the term "treating asthma" is meant curing asthma, causing the symptoms of asthma to diminish, ablating or otherwise alleviating the disease.

The term "modulating CD23 activity" as used herein means inhibiting (decreasing) the level of activity of CD23 protein in a cell. CD23 activity can be modulated by modification of the expression levels and/or activity of CD23 protein, or by modification of the level of CD23 gene transcription.

By the terms "CD23 antagonist" or "FcεRII antagonist" as used herein, is meant any natural or synthetic composition or compound which is capable of inhibiting the expression of CD23 or FcεRII protein on an airway smooth muscle cell, which inhibition prevents binding of IgE to the receptor protein. Preferably the CD23 antagonist is siRNA.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting CD23 mRNA may be between 15-35 nucleotides in length, and more typically about 21 nucleotides in length. A list of candidate siRNAs are provided in Table I.

Biological macromolecules include siRNA, shRNA, antisense oligonucleotides, peptides, peptide/DNA complexes, and any nucleic acid based molecule which exhibits the capacity to inhibit the activity of CD23 encoding nucleic acids or variants of SEQ ID NO: 1. As used herein, and in Li et al., CD23 antagonists may include short hairpin RNA molecules (shRNA). Typically, shRNA molecules consist of short complementary sequences separated by a small loop sequence wherein one of the sequences is complimentary to the gene target as provided in U.S. Application Publication No. 20050032733.

The term "intermediate", when used in reference to an siRNA, means one strand, either the sense or antisense strand or a portion thereof, of a double stranded siRNA. For convenience of discussion, the terms "sense" strand (or "plus" strand) and "antisense" strand (or "minus" strand) are used herein as they relate, for example, to an mRNA molecule, wherein the sense (plus) strand contains the information for encoding a peptide and an antisense (minus) strand would be complementary thereto. It should be recognized that, in fact, an antisense mRNA sequence is generally not produced in a cell. However, it should be further recognized that an siRNA need not necessarily be directed against an mRNA molecule but can be directed against any RNA molecule, including any endogenous or exogenous RNA in a cell or sample. For example, an siRNA can be directed against a structural RNA molecule such as a ribosomal RNA or small nuclear RNA (snRNA) molecules such as those involved in a spliceosome complex; a nucleotide sequence of transcribed intron, as occurs in a heterogeneous nuclear RNA (hnRNA); an X-chromosome modifier; or a microRNA.

The term "gene transcription" as it is used herein means a process whereby one strand of a DNA molecule is used as a template for synthesis of a complementary RNA by RNA polymerase.

The term "gene knockdown" as used herein refers to the reduction in the activity of a gene. The terms "gene silencing" and "gene inactivation" are considered to have the same meaning as the terms are used herein.

The term "DNA" as used herein refers to polynucleotide molecules, segments or sequences and is used herein to refer to a chain of nucleotides, each containing the sugar deoxyribose and one of the four adenine (A), guanine (G) thymine (T) or cytosine (C).

The term "RNA" as used herein refers to polynucleotide molecules, segments or sequences and is used herein to refer to a chain of nucleotides each containing the sugar ribose and one of the four adenine (A), guanine (G) uracil (U) or cytosine (C).

As used herein, "target mRNA" means human CD23 mRNA, mutant or alternative splice forms of human CD23 mRNA, or mRNA from cognate CD23 genes.

The term "oligonucleotide" or "oligo" as used herein means a short sequence of DNA or DNA derivatives typically 8 to 35 nucleotides in length, primers, or probes. An oligonucleotide can be derived synthetically, by cloning or by amplification. An oligo is defined as a nucleic acid molecule comprised of two or more ribo- or deoxyribonucleotides, preferably more than three. The exact size of the oligonucleotide will depend on various factors and on the particular application and use of the oligonucleotide. The term "derivative" is intended to include any of the above described variants when comprising an additional chemical moiety not normally a part of these molecules. These chemical moieties can have varying purposes including, improving solubility, absorption, biological half life, decreasing toxicity and eliminating or decreasing undesirable side effects.

The term "specifically hybridize" as used herein means that under appropriate conditions a probe made or a nucleic acid sequence such as an siRNA oligo hybridizes, duplexes or binds only to a particular target DNA or RNA sequence present in a cell or preparation of DNA or RNA. A probe sequence such as an siRNA sequence specifically hybridizes to a target sequence when the base sequence of the probe nucleic acid and the target sequence are complimentary to one another. The target sequence and the probe sequence do not have to be exactly complimentary to one another in order for the probe sequence to specifically hybridize. It is understood that specific hybridization can occur when the target and probe sequences are not exactly complimentary to one another and specific hybridization can occur when up only about 80% of the bases are complimentary to one another. Preferably, it is understood that in specific hybridizations probe and target sequence have 80% comprehensibility to one another. For discussions on hybridization see for example, Current Protocols in Molecular Biology, F. Ausubel et al., (ed.) Greene Publishing and Wiley-Interscience, New York (July, 2002).

"Peptide" and "polypeptide" are used interchangeably herein and refer to a compound made up of a chain of amino acid residues linked by peptide bonds. The sequence for peptides is given in the order from the amino terminus to the carboxyl terminus. A peptide or peptide fragment is "derived from" a parent peptide or polypeptide if it has the amino acid sequence that is identical or homologous to the amino acid sequence of the parent peptide or polypeptide.

The phrase "Nucleic acid" or "nucleic acid molecule" or "polynucleotide" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated.

A "vector" is a replicon, such as a plasmid, cosmid, bacmid, phage or virus, to which another genetic sequence or element (either DNA or RNA) may be attached so as to bring about the replication of the attached sequence or element.

The terms "transform", "transfect", "transduce", shall refer to any method or means by which a nucleic acid is introduced into a cell or host organism and may be used interchangeably to convey the same meaning. Such methods include, but are not limited to, tethering of membrane permeant peptides (e.g. Tat-peptide tethering), transfection, electroporation, microinjection, PEG-fusion and the like.

A "membrane permeant peptide sequence" refers to a peptide sequence which is able to facilitate penetration and entry of the CD23 inhibitor across the cell membrane. Exemplary peptides include with out limitation, the signal sequence from Karposi fibroblast growth factor exemplified herein, the HIV that peptide (Vives et al., J Biol. Chem., 272:16010-16017, 1997), Nontoxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

The term "aerosol formulation" refers to a pharmaceutical composition suitable for administration through the respiratory system or nasal passages. Similarly, the term "aerosol administration" is intended to refer to a mode of administering an aerosol formulation to the respiratory system or nasal passages.

The term "functional" as used herein implies that the nucleic or amino acid sequence is functional for the recited assay or purpose.

As used herein, the term "pharmaceutically-acceptable carrier" means a chemical composition with which an appropriate siRNA, may be combined and which, following the combination, can be used to administer the siRNA to a patient. The amount of the siRNA composition administered is sufficient to prevent, diminish or alleviate the asthmatic state. The pharmaceutical compositions useful for practicing the invention may be administered to deliver a dose of between about 1 ng/kg and about 100 mg/kg of patient body weight. Suitable amounts of the siRNA for administration include doses which are high enough to have the desired effect without concomitant adverse effects.

In the practice of the methods of the invention, a composition containing CD23 siRNA is administered to a patient in a sufficient amount to prevent, diminish or alleviate an asthmatic state in the individual. Patients to be treated include children and adults who have atopic (allergic) asthma. This constitutes the vast majority of asthmatic individuals.

There are several ways to administer the siRNA of the invention to in vivo to treat asthma including, but not limited to, naked siRNA delivery, siRNA conjugation and delivery, liposome carrier-mediated delivery, polymer carrier delivery, nanoparticle compositions, plasmid-based methods, and the use of viruses.

siRNA composition of the invention can comprise a delivery vehicle, including liposomes, for administration to a subject, carriers and diluents and their salts, and/or can be present in pharmaceutically acceptable formulations. This can be necessary to allow the siRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

Other carriers for the delivery of siRNA intra-nasally include a mixture of PBS and Oligofectamine as described in Tompkins et al., PNAS (2004) 101:8682-8686), and siRNA can be delivered with D5W (5% D-glucose in water) which has been used to achieve knockdown of SARS coronavirus RNA in Li et al., Nat. Med. (2005) 11:944-951.

The frequency of administration of the siRNA to a patient will also vary depending on several factors including, but not limited to, the type and severity of the asthma to be treated, the route of administration, the age and overall health of the individual, the nature of the siRNA, etc. It is contemplated that the frequency of administration of the siRNA to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate siRNA, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate siRNA to a patient according to the methods of the invention. The use of nanoparticles to deliver siRNAs, as well as cell membrane permeable peptide carriers that can be used are described in Crombez et al., Biochemical Society Transactions v 35: p 44 (2007).

Preferably, the composition of the invention is administered to the human by a lung inhalation route, i.e., via a nebulizer, aerosolizer, or other lung inhalation device.

An siRNA may be administered in conjunction with other compounds which are used to treat asthma. Such compounds include, but are not limited to, corticosteroids, sodium cromolyn, phosphodiesterase inhibitors, leukotriene modifiers, anti-cholinergic agents, and rapid relief medications that counteract bronchospasm, e.g., primarily beta-adrenergic agents. The choice of which additional compound to administer will vary depending upon any number of the same types of factors that govern the selection of dosage and administration frequency of the siRNA. Selection of these types of compounds for use in conjunction with an siRNA for practice of the method of the invention is well within the skill of those in the art.

The term "delivery" as used herein refers to the introduction of foreign molecule (i.e. nucleic acid small molecule inhibitor) in cells.

The term "treating" as used herein means the prevention, reduction, partial or complete alleviation or cure of a disease.

The term "administration" as used herein means the introduction of a foreign molecule (i.e. nucleic acid, small molecule inhibitor) into a cell. The term is intended to be synonymous with the term "Delivery".

As used herein, an "effective amount" of the siRNA is an amount sufficient to cause siRNA-mediated degradation of the target mRNA, or an amount sufficient to inhibit the asthma symptoms in a subject.

As disclosed herein, CD23 siRNA is effective at reducing a sign or symptom of asthma and thus is useful for the treatment thereof.

II. Pharmaceutical Compositions:

Methods of the invention directed to treating asthma involve the administration of CD23 siRNA in a pharmaceutical composition. CD23 siRNA is administered to an individual as a pharmaceutical composition comprising CD23 siRNA and a pharmaceutically acceptable carrier. Pharmaceutically acceptable carriers are well known in the art and include aqueous solutions such as physiologically buffered saline, other solvents or vehicles such as glycols, glycerol, oils such as olive oil or injectable organic esters.

A pharmaceutically acceptable carrier can contain physiologically acceptable compounds that act, for example, to stabilize the CD23 siRNA or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the CD23 siRNA.

One skilled in the art appreciates that a pharmaceutical composition comprising CD23 siRNA can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intra-tracheally (i.t.), or intra-articularly or by passive or facilitated absorption, and most preferably, using a nasal spray or inhalant.

A pharmaceutical composition comprising CD23 siRNA inhibitor also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

The pharmaceutical preparation comprises a siRNA targeting CD23 or an expression vector encoding for an siRNA targeting CD23. Such pharmaceutical preparations can be administered to a patient for treating asthma and reducing IgE binding.

Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

A formulated siRNA composition can be a composition comprising one or more siRNA molecules or a vector encoding one or more siRNA molecules independently or in combination with a cationic lipid, a neutral lipid, and/or a polyethyleneglycol-diacylglycerol (PEG-DAG) or PEG-cholesterol (PEG-Chol) conjugate. Non-limiting examples of expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500-505.

A lipid nanoparticle composition is a composition comprising one or more biologically active molecules independently or in combination with a cationic lipid, a neutral lipid, and/or a polyethyleneglycol-diacylglycerol (i.e., polyethyleneglycol diacylglycerol (PEG-DAG), PEG-cholesterol, or PEG-DMB) conjugate. In one embodiment, the biologically active molecule is encapsulated in the lipid nanoparticle as a result of the process of providing and aqueous solution comprising a biologically active molecule of the invention (i.e., siRNA), providing an organic solution comprising lipid nanoparticle, mixing the two solutions, incubating the solutions, dilution, ultrafiltration, resulting in concentrations suitable to produce nanoparticle compositions.

Nucleic acid molecules can be administered to cells by incorporation into other vehicles, such as biodegradable polymers, hydrogels, cyclodextrins. (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722)

Cationic lipids and polymers are two classes of non-viral siRNA delivery which can form complexes with negatively charged siRNA. The self-assembly PEG-ylated polycation polyethylenimine (PEI) has also been used to condense and protect siRNAs (Schiffelers et al., 2004, Nuc Acids Res. 32: 141-110). The siRNA complex can be condensed into a nanoparticle to allow efficient uptake of the siRNA through endocytosis. Also, the nucleic acid-condensing property of protamine has been combined with specific antibodies to deliver siRNAs and can be used in the invention (Song et al., 2005, Nat Biotech. 23:709-717).

Administration of CD23 siRNA by inhalation is a particularly preferred means of treating an individual having asthma. One skilled in the art would recognize that CD23 siRNA can be suspended or dissolved in an appropriate pharmaceutically acceptable carrier and administered, for example, directly into the lungs using a nasal spray or inhalant.

Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the nucleic acid compositions of the invention can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight. Other methods for pulmonary delivery are described in, for example US Patent Application No. 20040037780, and U.S. Pat. Nos. 6,592,904; 6,582,728; 6,565,885, all incorporated by reference herein.

A pharmaceutical composition comprising CD23 siRNA can be administered as an aerosol formulation which contains the inhibitor in dissolved, suspended or emulsified form in a propellant or a mixture of solvent and propellant. The aerosolized formulation is then administered through the respiratory system or nasal passages.

An aerosol formulation used for nasal administration is generally an aqueous solution designed to be administered to the nasal passages in drops or sprays. Nasal solutions are generally prepared to be similar to nasal secretions and are generally isotonic and slightly buffered to maintain a pH of about 5.5 to about 6.5, although pH values outside of this range can additionally be used. Antimicrobial agents or preservatives can also be included in the formulation.

An aerosol formulation used for inhalations and inhalants is designed so that the CD23 siRNA is carried into the respiratory tree of the patient administered by the nasal or oral respiratory route. Inhalation solutions can be administered, for example, by a nebulizer. Inhalations or insufflations, comprising finely powdered or liquid drugs, are delivered to the respiratory system as a pharmaceutical aerosol of a solution or suspension of the drug in a propellant.

An aerosol formulation generally contains a propellant to aid in disbursement of the CD23 siRNA. Propellants can be liquefied gases, including halocarbons, for example, fluorocarbons such as fluorinated chlorinated hydrocarbons, hydrochlorofluorocarbons, and hydrochlorocarbons as well as hydrocarbons and hydrocarbon ethers (Remington's Pharmaceutical Sciences 18th ed., Gennaro, A. R., ed., Mack Publishing Company, Easton, Pa. (1990)).

Halocarbon propellants useful in the invention include fluorocarbon propellants in which all hydrogens are replaced with fluorine, hydrogen-containing fluorocarbon propellants, and hydrogen-containing chlorofluorocarbon propellants. Halocarbon propellants are described in Johnson, U.S. Pat. No. 5,376,359, and Purewal et al., U.S. Pat. No. 5,776,434.

Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as numerous other ethers.

The CD23 siRNA can also be dispensed with a compressed gas. The compressed gas is generally an inert gas such as carbon dioxide, nitrous oxide or nitrogen.

An aerosol formulation of the invention can also contain more than one propellant. For example, the aerosol formulation can contain more than one propellant from the same class such as two or more fluorocarbons. An aerosol formulation can also contain more than one propellant from different classes. An aerosol formulation can contain any combination of two or more propellants from different classes, for example, a fluorohydrocarbon and a hydrocarbon.

Effective aerosol formulations can also include other components, for example, ethanol, isopropanol, propylene glycol, as well as surfactants or other components such as oils and detergents (Remington's Pharmaceutical Sciences, 1990; Purewal et al., U.S. Pat. No. 5,776,434). These aerosol components can serve to stabilize the formulation and lubricate valve components.

The aerosol formulation can be packaged under pressure and can be formulated as an aerosol using solutions, suspensions, emulsions, powders and semisolid preparations. A solution aerosol consists of a solution of an active ingredient such as CD23 siRNA in pure propellant or as a mixture of propellant and solvent. The solvent is used to dissolve the active ingredient and/or retard the evaporation of the propellant. Solvents useful in the invention include, for example, water, ethanol and glycols. A solution aerosol contains the active ingredient peptide and a propellant and can include any combination of solvents and preservatives or antioxidants.

An aerosol formulation can also be a dispersion or suspension. A suspension aerosol formulation will generally contain a suspension of an effective amount of the CD23 siRNA and a dispersing agent. Dispersing agents useful in the invention include, for example, sorbitan trioleate, oleyl alcohol, oleic acid, lecithin and corn oil. A suspension aerosol formulation can also include lubricants and other aerosol components.

An aerosol formulation can similarly be formulated as an emulsion. An emulsion can include, for example, an alcohol such as ethanol, a surfactant, water and propellant, as well as the active ingredient, CD23 siRNA. The surfactant can be nonionic, anionic or cationic. One example of an emulsion can include, for example, ethanol, surfactant, water and propellant. Another example of an emulsion can include, for example, vegetable oil, glyceryl monostearate and propane.

An aerosol formulation containing CD23 siRNA will generally have a minimum of 90% of the particles in inhalation products between about 0.5 and about 10 µm to maximize delivery and deposition of the CD23 siRNA to respiratory fluids. In particular, the particle size can be from about 3 to about 6 µm.

In order to treat an individual having asthma, to alleviate a sign or symptom of the disease, CD23 siRNA should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of CD23 siRNA required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having asthma.

The effective dose of CD23 siRNA will depend on the mode of administration, and the weight of the individual being treated. The dosages described herein are generally those for an average adult but can be adjusted for the treatment of children. The dose will generally range from about 0.001 mg to about 1000 mg.

The concentration of CD23 siRNA in a particular formulation will depend on the mode and frequency of administration. A given daily dosage can be administered in a single dose or in multiple doses so long as the CD23 siRNA concentration in the formulation results in the desired daily dosage. One skilled in the art can adjust the amount of CD23 siRNA in the formulation to allow administration of a single dose or in multiple doses that provide the desired concentration of CD23 siRNA over a given period of time.

In an individual suffering from asthma, in particular a more severe form of the disease, administration of CD23 siRNA can be particularly useful when administered in combination, for example, with a conventional agent for treating such a disease. The skilled artisan would administer CD23 siRNA, alone or in combination with a second agent, based on the clinical signs and symptoms exhibited by the individual and would monitor the effectiveness of such treatment using routine methods such as pulmonary function determination, radiologic, immunologic or, where indicated, histopathologic methods.

CD23 siRNA can be administered in combination with steroidal anti-inflammatory agents including corticosteroids, for example, dexamethasone, beclomethasone, fluticasone, triamcinolone and budesonide. CD23 siRNA can also be administered in combination with non-steroidal anti-inflammatory agents such as indomethacin, ibuprofen, naproxen, diclofenac, sulindac, oxaprozin, diflunisal, bromfenac, piroxicam, etodolac and fenoprofen. Additionally, the CD23 siRNAs of the invention can be administered with anti-inflammatory agents such as sodium cromolyn, IgE inhibitors, phosphodiesterase inhibitors, methylxanthines, beta-adrenergic agents, and leukotriene modifiers. When CD23 siRNA is used with another anti-inflammatory agent, the CD23 siRNA can generally be administered at a lower dosage. For example, CD23 siRNA can be administered at a dose of less than 0.1 mg per day in combination with another anti-inflammatory agent.

When CD23 siRNA is administered in combination with one or more other anti-inflammatory agent, the CD23 siRNA and other anti-inflammatory agent can be co-administered in the same formulation. Alternatively, the CD23 siRNA and other anti-inflammatory agent can be administered simultaneously in separate formulations. In addition, the CD23 siRNA can be administered in separate formulations, where the separate formulations are not administered simultaneously but are administered during the same period of treatment, for example, during a daily or weekly period of treatment.

Administration of the pharmaceutical preparation is preferably in an "effective amount" this being sufficient to show benefit to the individual. This amount prevents, alleviates, abates, or otherwise reduces the severity of asthma symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

As mentioned previously, a preferred embodiment of the invention comprises aerosolized delivery of the CD23 siRNA to the lungs of a patient in need thereof. As stated hereinabove, candidate siRNA compositions for use in the invention are provided in Table I. The sequences in Table I include several siRNA duplexes (i.e., sense and antisense sequences for a CD23 target region), as well as several sequences of 'sense' strand alone (SEQ ID NOs: 101-247). Those of skill in the art can determine the sequence of an antisense siRNA strand based on the disclosure of the sense strand, and will appreciate the difference between "U" and "T" designations in the sequences which correspond to RNA and DNA molecules, respectively. Also, methods of using known inhibitors of CD23 to treat asthma are also provided. For example, shRNA constructs have been shown to be effective to inhibit CD23 in the intestine as disclosed in Li et al. (Gastroenterology (2007) 133:1905-1915); these constructs also have utility in the present methods and are: CGCTGAACAGCAGAGAT-TGAAA (SEQ ID NO: 15) and CCCACGGATGCGGC-CCCGTGCC (SEQ ID NO: 16). Santa Cruz Biotechnology's CD23 siRNAs can also be used in the methods of the present invention (Santa Cruz Catalog Nos. sc-29976 and sc-29977), as well as other commercially available CD23 siRNA constructs, which include, but are not limited to Dharmacon's Catalog Nos. L-016242-00, LQ-016242-00, M-016242-00, J-016242-01, J-016242-02, J-016242-03, J-016242-04, J-016242-05, J-016242-06, J-016242-07, and J-016242-08.

TABLE I

Candidate CD23 siRNA molecules

| | |
|---|---|
| GGUCAAUAUUCAGAGAUCGtt - sense strand (s) | SEQ ID NO: 17 |
| CGAUCUCUGAAUAUUGACCtt - antisense strand (as) | SEQ ID NO: 18 |
| UAUUCAGAGAUCGAGGAGCtt - s | SEQ ID NO: 19 |
| GCUCCUCGAUCUCUGAAUAtt - as | SEQ ID NO: 20 |
| AACAGCUGGAAGAGAGGGCtt - s | SEQ ID NO: 21 |
| GCCCUCUCUUCCAGCUGUUtt - as | SEQ ID NO: 22 |
| CAGCUGGAAGAGAGGGCUGtt - s | SEQ ID NO: 23 |

TABLE I-continued

Candidate CD23 siRNA molecules

| | |
|---|---|
| CAGCCCUCUCUUCCAGCUGtt - as | SEQ ID NO: 24 |
| GAGAGGGCUGCCCGGAACGtt - s | SEQ ID NO: 25 |
| CGUUCCGGGCAGCCCUCUCtt - as | SEQ ID NO: 26 |
| CGUCUCUCAAGUUCCAAGtt - s | SEQ ID NO: 27 |
| CUUGGAAACUUGAGAGACGtt - as | SEQ ID NO: 28 |
| GUUUCCAAGAACUUGGAAAtt - s | SEQ ID NO: 29 |
| UUUCCAAGUUCUUGGAAACtt - as | SEQ ID NO: 30 |
| GAACUUGGAAAGCCACCAtt - s | SEQ ID NO: 31 |
| GUGGUGGCUUUCCAAGUUCtt - as | SEQ ID NO: 32 |
| CUUGGAAAGCCACCACGGUtt - s | SEQ ID NO: 33 |
| ACCGUGGUGGCUUUCCAAGtt - as | SEQ ID NO: 34 |
| AGCCACCACGGUGACCAGAtt - s | SEQ ID NO: 35 |
| UCUGGUCACCGUGGUGGCUtt - as | SEQ ID NO: 36 |
| AUCCCAGUCCACGCAGAUUtt - s | SEQ ID NO: 37 |
| AAUCUGCGUGGACUGGGAUtt - as | SEQ ID NO: 38 |
| CUGGAGGAACUUCGAGCUGtt - s | SEQ ID NO: 39 |
| CAGCUCGAAGUUCCUCCAGtt - as | SEQ ID NO: 40 |
| CUUCGAGCUGAACAGCAGAtt - s | SEQ ID NO: 41 |
| UCUGCUGUUCAGCUCGAAGtt - as | SEQ ID NO: 42 |
| CAGCAGAGAUUGAAAUCUCtt - s | SEQ ID NO: 43 |
| GAGAUUUCAAUCUCUGCUGtt - as | SEQ ID NO: 44 |
| AUCUCAGGACUUGGAGCUGtt - s | SEQ ID NO: 45 |
| CAGCUCCAAGUCCUGAGAUtt - as | SEQ ID NO: 46 |
| CCUGAACGGGCUUCAAGCAtt - s | SEQ ID NO: 47 |
| UGCUUGAAGCCCGUUCAGGtt - as | SEQ ID NO: 48 |
| CGGGCUUCAAGCAGAUCUGtt - s | SEQ ID NO: 49 |
| CAGAUCUGCUUGAAGCCCGtt - as | SEQ ID NO: 50 |
| GCAGAUCUGAGCAGCUUCAtt - s | SEQ ID NO: 51 |
| UGAAGCUGCUCAGAUCUGCtt - as | SEQ ID NO: 52 |
| GUCCCAGGAAUUGAACGAGtt - s | SEQ ID NO: 53 |
| CUCGUUCAAUUCCUGGGACtt - as | SEQ ID NO: 54 |
| UUGAACGAGAGGAACGAAGtt - s | SEQ ID NO: 55 |
| CUUCGUUCCUCUCGUUCAAtt - as | SEQ ID NO: 56 |
| CGAGAGGAACGAAGCUUCAtt - s | SEQ ID NO: 57 |
| UGAAGCUUCGUUCCUCUCGtt - as | SEQ ID NO: 58 |
| GCUUCAGAUUUGCUGGAAAtt - s | SEQ ID NO: 59 |
| UUUCCAGCAAAUCUGAAGCtt - as | SEQ ID NO: 60 |
| AGACUCCGGGAGGAGGUGAtt - s | SEQ ID NO: 61 |
| UCACCUCCUCCCGGAGUCUtt - as | SEQ ID NO: 62 |
| AGCUAAGGAUGGAGUUGCAtt - s | SEQ ID NO: 63 |
| UGCAACUCCAUCCUUAGCUtt - as | SEQ ID NO: 64 |
| GGAUGGAGUUGCAGGUGUCtt - s | SEQ ID NO: 65 |
| GACACCUGCAACUCCAUCCtt - as | SEQ ID NO: 66 |
| CACGUGCCCUGAAAAGUGGtt - s | SEQ ID NO: 67 |
| CCACUUUUCAGGGCACGUGtt - as | SEQ ID NO: 68 |
| AAGUGGAUCAAUUUCCAACtt - s | SEQ ID NO: 69 |
| GUUGGAAAUUGAUCCACUUtt - as | SEQ ID NO: 70 |
| GUGGAUCAAUUUCCAACGGtt - s | SEQ ID NO: 71 |
| CCGUUGGAAAUUGAUCCACtt - as | SEQ ID NO: 72 |
| UUUCCAACGGAAGUGCUACtt - s | SEQ ID NO: 73 |
| GUAGCACUUCCGUUGGAAAtt - as | SEQ ID NO: 74 |
| CGGAAGUGCUACUACUUCGtt - s | SEQ ID NO: 75 |
| CGAAGUAGUAGCACUUCCGtt - as | SEQ ID NO: 76 |
| GUGCUACUACUUCGGCAAGtt - s | SEQ ID NO: 77 |
| CUUGCCGAAGUAGUAGCACtt - as | SEQ ID NO: 78 |
| GGGCACCAAGCAGUGGGUCtt - s | SEQ ID NO: 79 |
| GACCCACUGCUUGGUGCCCtt - as | SEQ ID NO: 80 |
| GCAGUGGGUCCACGCCCGGtt - s | SEQ ID NO: 81 |
| CCGGGCGUGGACCCACUGCtt - as | SEQ ID NO: 82 |
| GGGCAGCUGGUCAGCAUCCtt - s | SEQ ID NO: 83 |
| GGAUGCUGACCAGCUGCCCtt - as | SEQ ID NO: 84 |
| GCAUGCCAGCCACACCGGCtt - s | SEQ ID NO: 85 |
| GCCGGUGUGGCUGGCAUGCtt - as | SEQ ID NO: 86 |
| CUUGGACCUGAAGGGGAGtt - s | SEQ ID NO: 87 |
| CUCCCCCUUCAGGUCCAAGtt - as | SEQ ID NO: 88 |
| GGGGGAGUUUAUCUGGGUGtt - s | SEQ ID NO: 89 |
| CACCCAGAUAAACUCCCCCtt - as | SEQ ID NO: 90 |
| CUGGGCUCCAGGGGAGCCCtt - s | SEQ ID NO: 91 |
| GGGCUCCCCUGGAGCCCAGtt - as | SEQ ID NO: 92 |
| CGACGCCUUCUGCGACCGUtt - s | SEQ ID NO: 93 |
| ACGGUCGCAGAAGGCGUCGtt - as | SEQ ID NO: 94 |
| GCUGGGCGCCUGGGUGUGCtt - s | SEQ ID NO: 95 |
| GCACACCCAGGCGCCCAGCtt - as | SEQ ID NO: 96 |
| GGUUCCGCGGAGUCCAUGGtt - s | SEQ ID NO: 97 |
| CCAUGGACUCCGCGGAACCtt - as | SEQ ID NO: 98 |
| GACCAGACCCUGACGGCCGtt - s | SEQ ID NO: 99 |
| CGGCCGUCAGGGUCUGGUCtt - as | SEQ ID NO: 100 |
| GGCTGGGCTGCTGACTCTGtt - s | SEQ ID NO: 101 |

TABLE I-continued

Candidate CD23 siRNA molecules

| Sequence | SEQ ID NO |
|---|---|
| GCTGGGCTGCTGACTCTGCtt - s | SEQ ID NO: 102 |
| CTGGGCTGCTGACTCTGCTtt - s | SEQ ID NO: 103 |
| GGGCTGCTGACTCTGCTTCtt - s | SEQ ID NO: 104 |
| CACCACACAGAGTCTAAAAtt - s | SEQ ID NO: 105 |
| CCACACAGAGTCTAAAACAtt - s | SEQ ID NO: 106 |
| CACAGAGTCTAAAACAGCTtt - s | SEQ ID NO: 107 |
| CAGAGTCTAAAACAGCTGGtt - s | SEQ ID NO: 108 |
| GAGTCTAAAACAGCTGGAAtt - s | SEQ ID NO: 109 |
| GTCTAAAACAGCTGGAAGAtt - s | SEQ ID NO: 110 |
| AAACAGCTGGAAGAGAGGGtt - s | SEQ ID NO: 111 |
| AACAGCTGGAAGAGAGGGCtt - s | SEQ ID NO: 112 |
| ACAGCTGGAAGAGAGGGCTtt - s | SEQ ID NO: 113 |
| CAGCTGGAAGAGAGGGCTGtt - s | SEQ ID NO: 114 |
| AGAGAGGGCTGCCCGGAACtt - s | SEQ ID NO: 115 |
| ACGTCTCTCAAGTTTCCAAtt - s | SEQ ID NO: 116 |
| CGTCTCTCAAGTTTCCAAGtt - s | SEQ ID NO: 117 |
| AGTTTCCAAGAACTTGGAAtt - s | SEQ ID NO: 118 |
| GTTTCCAAGAACTTGGAAAtt - s | SEQ ID NO: 119 |
| AGAACTTGGAAAGCCACCAtt - s | SEQ ID NO: 120 |
| GAACTTGGAAAGCCACCACtt - s | SEQ ID NO: 121 |
| ACTTGGAAAGCCACCACGGtt - s | SEQ ID NO: 122 |
| CTTGGAAAGCCACCACGGTtt - s | SEQ ID NO: 123 |
| AAGCCACCACGGTGACCAGtt - s | SEQ ID NO: 124 |
| AGCCACCACGGTGACCAGAtt - s | SEQ ID NO: 125 |
| GCCACCACGGTGACCAGATtt - s | SEQ ID NO: 126 |
| CCACGGTGACCAGATGGCGtt - s | SEQ ID NO: 127 |
| CGGTGACCAGATGGCGCAGtt - s | SEQ ID NO: 128 |
| CCAGATGGCGCAGAAATCCtt - s | SEQ ID NO: 129 |
| GATGGCGCAGAAATCCCAGtt - s | SEQ ID NO: 130 |
| TGGCGCAGAAATCCCAGTCtt - s | SEQ ID NO: 131 |
| GAAATCCCAGTCCACGCAGtt - s | SEQ ID NO: 132 |
| AATCCCAGTCCACGCAGATtt - s | SEQ ID NO: 134 |
| ATCCCAGTCCACGCAGATTtt - s | SEQ ID NO: 135 |
| TCCCAGTCCACGCAGATTTtt - s | SEQ ID NO: 136 |
| GTCCACGCAGATTTCACAGtt - s | SEQ ID NO: 137 |
| CGCAGATTTCACAGGAACTtt - s | SEQ ID NO: 138 |
| GATTTCACAGGAACTGGAGtt - s | SEQ ID NO: 139 |
| TTTCACAGGAACTGGAGGAtt - s | SEQ ID NO: 140 |
| CAGGAACTGGAGGAACTTCtt - s | SEQ ID NO: 141 |
| GGAACTGGAGGAACTTCGAtt - s | SEQ ID NO: 142 |
| ACTGGAGGAACTTCGAGCTtt - s | SEQ ID NO: 143 |
| CTGGAGGAACTTCGAGCTGtt - s | SEQ ID NO: 144 |
| GGAACTTCGAGCTGAACAGtt - s | SEQ ID NO: 145 |
| ACTTCGAGCTGAACAGCAGtt - s | SEQ ID NO: 146 |
| CTTCGAGCTGAACAGCAGAtt - s | SEQ ID NO: 147 |
| ACCTGAACGGGCTTCAAGCtt - s | SEQ ID NO: 148 |
| CCTGAACGGGCTTCAAGCAtt - s | SEQ ID NO: 149 |
| ACGGGCTTCAAGCAGATCTtt - s | SEQ ID NO: 150 |
| CGGGCTTCAAGCAGATCTGtt - s | SEQ ID NO: 151 |
| AGCAGATCTGAGCAGCTTCtt - s | SEQ ID NO: 152 |
| GCAGATCTGAGCAGCTTCAtt - s | SEQ ID NO: 153 |
| GATCTGAGCAGCTTCAAGTtt - s | SEQ ID NO: 154 |
| TCTGAGCAGCTTCAAGTCCtt - s | SEQ ID NO: 155 |
| CTGAGCAGCTTCAAGTCCCtt - s | SEQ ID NO: 156 |
| GCAGCTTCAAGTCCCAGGAtt - s | SEQ ID NO: 157 |
| GCTTCAAGTCCCAGGAATTtt - s | SEQ ID NO: 158 |
| AGTCCCAGGAATTGAACGAtt - s | SEQ ID NO: 159 |
| GTCCCAGGAATTGAACGAGtt - s | SEQ ID NO: 160 |
| ATTGAACGAGAGGAACGAAtt - s | SEQ ID NO: 161 |
| TTGAACGAGAGGAACGAAGtt - s | SEQ ID NO: 162 |
| ACGAGAGGAACGAAGCTTCtt - s | SEQ ID NO: 163 |
| CGAGAGGAACGAAGCTTCAtt - s | SEQ ID NO: 164 |
| TTTGCTGGAAAGACTCCGGtt - s | SEQ ID NO: 165 |
| AAGACTCCGGGAGGAGGTGtt - s | SEQ ID NO: 166 |
| AGACTCCGGGAGGAGGTGAtt - s | SEQ ID NO: 167 |
| GACTCCGGGAGGAGGTGACtt - s | SEQ ID NO: 168 |
| CTCCGGGAGGAGGTGACAAtt - s | SEQ ID NO: 169 |
| GGAGGTGACAAAGCTAAGGtt - s | SEQ ID NO: 170 |
| GGTGACAAAGCTAAGGATGtt - s | SEQ ID NO: 171 |
| CAAAGCTAAGGATGGAGTTtt - s | SEQ ID NO: 172 |
| AAGCTAAGGATGGAGTTGCtt - s | SEQ ID NO: 173 |
| AGCTAAGGATGGAGTTGCAtt - s | SEQ ID NO: 174 |
| GCTAAGGATGGAGTTGCAGtt - s | SEQ ID NO: 175 |
| AGGATGGAGTTGCAGGTGTtt - s | SEQ ID NO: 176 |
| GGATGGAGTTGCAGGTGTCtt - s | SEQ ID NO: 177 |
| TGGAGTTGCAGGTGTCCAtt - s | SEQ ID NO: 178 |
| GTTGCAGGTGTCCAGCGGCtt - s | SEQ ID NO: 179 |
| GGTGTCCAGCGGCTTTGTGtt - s | SEQ ID NO: 180 |

TABLE I-continued

Candidate CD23 siRNA molecules

| | |
|---|---|
| GCGGCTTTGTGTGCAACACtt - s | SEQ ID NO: 181 |
| ACACGTGCCCTGAAAAGTGtt - s | SEQ ID NO: 182 |
| CACGTGCCCTGAAAAGTGGtt - s | SEQ ID NO: 183 |
| CGTGCCCTGAAAAGTGGATtt - s | SEQ ID NO: 184 |
| AAAGTGGATCAATTTCCAAtt - s | SEQ ID NO: 185 |
| AAGTGGATCAATTTCCAACtt - s | SEQ ID NO: 186 |
| AGTGGATCAATTTCCAACGtt - s | SEQ ID NO: 187 |
| GTGGATCAATTTCCAACGGtt - s | SEQ ID NO: 188 |
| TCAATTTCCAACGGAAGTGtt - s | SEQ ID NO: 189 |
| ATTTCCAACGGAAGTGCTAtt - s | SEQ ID NO: 190 |
| TTTCCAACGGAAGTGCTACtt - s | SEQ ID NO: 191 |
| ACGGAAGTGCTACTACTTCtt - s | SEQ ID NO: 192 |
| CGGAAGTGCTACTACTTCGtt - s | SEQ ID NO: 193 |
| AGTGCTACTACTTCGGCAAtt - s | SEQ ID NO: 194 |
| GTGCTACTACTTCGGCAAGtt - s | SEQ ID NO: 195 |
| CTACTTCGGCAAGGGCACCtt - s | SEQ ID NO: 196 |
| CTTCGGCAAGGGCACCAAGtt - s | SEQ ID NO: 197 |
| AGGGCACCAAGCAGTGGGTtt - s | SEQ ID NO: 198 |
| GGGCACCAAGCAGTGGGTCtt - s | SEQ ID NO: 199 |
| CGCCCGGTATGCCTGTGACtt - s | SEQ ID NO: 200 |
| TGCCTGTGACGACATGGAAtt - s | SEQ ID NO: 201 |
| CGACATGGAAGGGCAGCTGtt - s | SEQ ID NO: 202 |
| CATGGAAGGGCAGCTGGTCtt - s | SEQ ID NO: 203 |
| TGGAAGGGCAGCTGGTCAGtt - s | SEQ ID NO: 204 |
| AGGGCAGCTGGTCAGCATCtt - s | SEQ ID NO: 205 |
| GGGCAGCTGGTCAGCATCCtt - s | SEQ ID NO: 206 |
| AGCTGGTCAGCATCCACAGtt - s | SEQ ID NO: 207 |
| GCTGGTCAGCATCCACAGCtt - s | SEQ ID NO: 208 |
| CAGCCCGGAGGAGCAGGACtt - s | SEQ ID NO: 209 |
| GGAGCAGGACTTCCTGACCtt - s | SEQ ID NO: 210 |
| GCAGGACTTCCTGACCAAGtt - s | SEQ ID NO: 211 |
| GGACTTCCTGACCAAGCATtt - s | SEQ ID NO: 212 |
| CTTCCTGACCAAGCATGCCtt - s | SEQ ID NO: 213 |
| CCAAGCATGCCAGCCACACtt - s | SEQ ID NO: 214 |
| AGCATGCCAGCCACACCGGtt - s | SEQ ID NO: 215 |
| GCCACACCGGCTCCTGGATtt - s | SEQ ID NO: 216 |
| CACCGGCTCCTGGATTGGCtt - s | SEQ ID NO: 217 |
| CCGGCTCCTGGATTGGCCTtt - s | SEQ ID NO: 218 |
| TTGGCCTTCGGAACTTGGAtt - s | SEQ ID NO: 219 |
| ACTTGGACCTGAAGGGGGAtt - s | SEQ ID NO: 220 |
| CTTGGACCTGAAGGGGAGtt - s | SEQ ID NO: 221 |
| CCTGAAGGGGAGTTTATCtt - s | SEQ ID NO: 222 |
| AGGGGGAGTTTATCTGGGTtt - s | SEQ ID NO: 223 |
| GGGGGAGTTTATCTGGGTGtt - s | SEQ ID NO: 224 |
| GTTTATCTGGGTGGATGGGtt - s | SEQ ID NO: 225 |
| TCTGGGTGGATGGGAGCCAtt - s | SEQ ID NO: 226 |
| TGGGAGCCACGTGGACTActt - s | SEQ ID NO: 227 |
| GCCACGTGGACTACAGCAAtt - s | SEQ ID NO: 228 |
| CGTGGACTACAGCAACTGGtt - s | SEQ ID NO: 229 |
| CTACAGCAACTGGGCTCCAtt - s | SEQ ID NO: 230 |
| CAGCAACTGGGCTCCAGGtt - s | SEQ ID NO: 231 |
| GGGCGAGGACTGCGTGATGtt - s | SEQ ID NO: 232 |
| GGACTGCGTGATGATGCGGtt - s | SEQ ID NO: 234 |
| CTGCGTGATGATGCGGGCtt - s | SEQ ID NO: 235 |
| ACGACGCCTTCTGCGACCGtt - s | SEQ ID NO: 236 |
| CGACGCCTTCTGCGACCGTtt - s | SEQ ID NO: 237 |
| CGCCTTCTGCGACCGTAAGtt - s | SEQ ID NO: 238 |
| GCGAAGGTTCCGCGGAGTCtt - s | SEQ ID NO: 239 |
| AGGTTCCGCGGAGTCCATGtt - s | SEQ ID NO: 240 |
| GGTTCCGCGGAGTCCATGtt - s | SEQ ID NO: 241 |
| GTCCATGGGACCTGATTCAtt - s | SEQ ID NO: 242 |
| TGGGACCTGATTCAAGACCtt - s | SEQ ID NO: 243 |
| CCTGATTCAAGACCAGACCtt - s | SEQ ID NO: 244 |
| TTCAAGACCAGACCCTGACtt - s | SEQ ID NO: 245 |
| CCCTCTGCCCCTCTCCACTtt - s | SEQ ID NO: 246 |
| CTCTTGAGCATGGATACAGtt - s | SEQ ID NO: 247 |

The following materials and methods are provided to facilitate practice of the present invention:

Materials: All chemicals were purchased from Sigma-Aldrich unless otherwise indicated. The human ASM cells were obtained from BioWhittaker, Inc.

Animals: Adult New Zealand White rabbits were used in this study, which was approved by the Biosafety and Animal Research Committee of the Joseph Stokes Research Institute at Children's Hospital of Philadelphia. The animals had no signs of respiratory disease for several weeks before the study, and their care and use were in accordance with the "Guide for the Care and Use of Laboratory Animals" prepared by the Institute of Laboratory Animal Resources, National Research Council.

Immunization protocol: Rabbits were actively immunized by an intra-peritoneal injection of 1 ml of an emulsion containing ovalbumin (OVA; 2.5 mg in PBS) mixed in equal part with adjuvant, administered each week for 3 weeks and, thereafter, every alternate week for a one month period. Non-immunized rabbits receiving injections with PBS alone served as controls. Thereafter, the rabbits were challenged by airway administration of a 3% solution of OVA. After approximately 15 to 20 min, the immunized rabbits exhibited active wheezing associated with nasal flaring, active contraction of the abdominal muscles during the expiratory phase of respiration, and prolongation of the expiration phase. These signs of an acute asthmatic reaction were not exhibited in the control rabbits. Approximately 40 ml of blood was then drawn via an ear vein from each of the immunized and control rabbits for preparation of asthmatic and non-asthmatic serum samples to be used for subsequent passive sensitization of ASM tissue segments isolated from naïve rabbits, as described below.

siRNA-mediated knockdown of CD23 in cultured ASM cells: Human ASM cells were grown in SmBm media supplemented with 10% FBS (BioWhittaker) and maintained throughout in a humidified incubator containing 5% $CO_2$ in air at 37° C. The experimental protocols involved seeding the cells into 6-well plates and, at ~40% confluency, the medium was replaced with the reduced serum-containing medium, Opti-MEM (Invitrogen). Separate preparations of cells were then transfected twice during a 24-hr interval with each of four different siRNA duplexes targeted against human CD23, using Oligofectamine (Invitrogen) as the transfection agent. The siRNA preparations were purchased from Applied Biosystems and comprised the following nucleotide sequences:

```
for siRNA ID #111062:
                                    (SEQ ID NO: 3)
5'-CGAAGCUUCAGAUUUGCUGtt-3' (sense)
and (SEQ ID NO: 4)
5'-CAGCAAAUCUGAAGCUUCGtt-3' (antisense);

for siRNA ID #106645:
                                    (SEQ ID NO: 5)
5'-GGUGACAAAGCUAAGGAUGtt-3' (sense)
and (SEQ ID NO: 6)
5'-CAUCCUUAGCUUUGUCACCtc-3' (antisense);

for siRNA ID #111060:
                                    (SEQ ID NO: 7)
5'-GGAAUUGAACGAGAGGAACtt-3' (sense)
and (SEQ ID NO: 8)
5'-GUUCCUCUCGUUCAAUUCCtg-3' (antisense);

for siRNA ID #106644:
                                    (SEQ ID NO: 9)
5'-GGAGGUGACAAAGCUAAGGtt-3' (sense)
and (SEQ ID NO: 10)
5'-CCUUAGCUUUGUCACCUCCtc-3' (antisense).
```

Additionally, cell preparations were also transfected with either a pool of these CD23-directed siRNA duplexes, a non-targeted negative control (scrambled) siRNA duplex, or a negative control duplex labeled with the fluorescein derivative, Cy™3, to visualize siRNA transfection efficiency. The siRNAs were applied to each well at a final concentration of 100 nM for each siRNA duplex. After 3 days, the cells were exposed for 12 hr to either vehicle alone or the pro-asthmatic cytokine, IL-13 (50 ng/ml), which is known to upregulate CD23 expression in human monocytes. The cells were subsequently examined for induced changes in mRNA expression of CD23a.

Detection of CD23 mRNA transcripts: Total RNA was extracted from the cultured ASM cells using the TRIzol method (Invitrogen), and cDNAs were isolated by RT-PCR using the SuperScript First Strand Synthesis System kit from Invitrogen, with the following oligonucleotide primer sets (Integrated DNA Technologies): for CD23a, (SEQ ID NO: 11) 5'-CACAATGGAGGAAGGTCAATATTCAG-3' (forward) and (SEQ ID NO: 12) 5'-TTGAGAGACGTTC-CGGGCAGCCCTCTCTTCCAGCTGTT-3' (reverse); and for β-actin, (SEQ ID NO: 13) 5'-GAGAAGAGCTAC-GAGCTGCCTGAC-3' (forward) and (SEQ ID NO: 14) 5'-CGGAGTACTTGCGCTCAGGAGGAG-3' (reverse). The reaction volume was 20 µl and cycling conditions used were 35 cycles of 30 sec denaturation at 95° C., followed by 30 sec annealing at 60° C. and elongation at 72° C. for 30 sec. Ex-Tag (Takara Biotechnology) was used as DNA polymerase.

Pharmacodynamic studies of constrictor and relaxation responsiveness in rabbit ASM tissues: Following initial sedation and subsequent general anesthesia with intramuscular injections of xylazine (10 mg/kg) and ketamine (50 mg/kg), respectively, rabbits were sacrificed with an intravenously administered overdose of sodium pentobarbital (100 mg/kg). The tracheae were excised via open thoracotomy, the loose connective tissue and epithelium were scraped and removed, and the tracheae were divided into 8 ring segments, each of 6-8 mm in length. Each airway segment was then incubated for 24 hr at room temperature with a 50% concentration of serum isolated from either the control or OVA-immunized rabbits in the presence of pretreatment with 2.0 nmol of either the scrambled siRNA duplex (serving as control) or the pool of four CD23 siRNA duplexes (i.e., each at 0.5 nmol). Thereafter, the tissues were placed in organ baths containing modified Krebs-Ringer solution aerated with 5% $CO_2$ in oxygen (pH of 7.35-7.40), and attached to force transducers to continuously monitor isometric tension. Cholinergic contractility was then assessed in the tissues following cumulative administration of acetylcholine (ACh) in final bath concentrations ranging from $10^{-9}$ to $10^{-3}$ M. The tissues were then repeatedly rinsed with fresh buffer, and relaxation dose-response curves to isoproterenol ($10^{-9}$-$10^{-4}$ M) were generated after the tissues were half-maximally contracted with their respective $ED_{50}$ doses of ACh. The constrictor and relaxation dose-response curves were analyzed with respect to each tissue's maximal isometric contractile force (Tmax) to ACh and maximal relaxation response (Rmax) to isoproterenol from the initial level of active cholinergic contraction.

Statistical analyses: Results are expressed as mean±SE values. Comparisons between groups were made using the Student's t-test (two-tailed) or ANOVA with Tukey's post-test analysis, where appropriate. A probability of <0.05 was considered statistically significant. Statistical analyses were conducted using the Prism computer program by GraphPad Software Inc.

It is understood that modifications which do not substantially affect the activity of the various embodiments of this invention are also provided within the definition of the invention provided herein. Accordingly, the following examples are provided to illustrate an embodiment of the invention. They are not intended to limit the scope of the invention in any way.

EXAMPLE 1

CD23 siRNA Delivery to Cultured Human ASM Cells

CD23-siRNA was examined for its ability to be delivered to airway smooth muscle cells. As shown in FIG. 1, (upper panel) the siRNA duplex is incorporated into ASM cells to a greater degree when Oligofectamine is used to deliver the constructs. FIG. 1 (middle panel) depicts the results of the direct administration and (lower panel) that Oligofectamine alone acts as a control.

These results demonstrate that human ASM cells can incorporate exogenously administered siRNA duplexes, however, the efficiency of siRNA transfection is greatly enhanced when using Oligofectamine as a transfection reagent.

EXAMPLE 2 siRNA-Mediated Inhibition of CD23 mRNA Expression in Cultured ASM Cells

Figure 2:
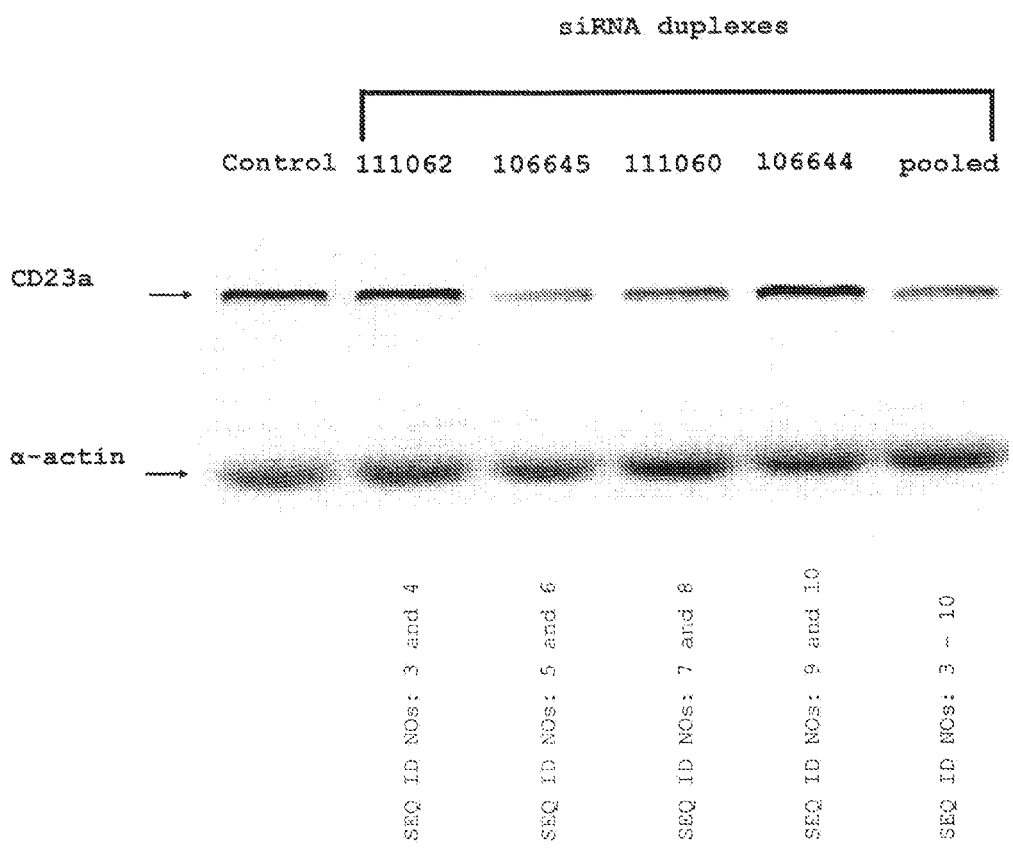

Given that ASM cells constitutively express CD23 mRNA, the effect of CD23 siRNA was tested using Oligofectamine-mediated delivery. To this end, the effectiveness of four siRNA preparations for inhibiting constitutive and IL-13-stimulated expression of CD23 mRNA in cultured human ASM cells was tested. The results in FIG. 2 show that siRNA constructs 111062 (SEQ ID NOs: 3 and 4), and 106644 (SEQ ID NOs: 9 and 10) have no effect on CD23 mRNA expression, however, siRNAs 106645 (SEQ ID NOs: 5 and 6) and 111060 (SEQ ID NOs: 7 and 8) show marked inhibition of CD23 mRNA (lanes 3 and 4).

Figure 3:
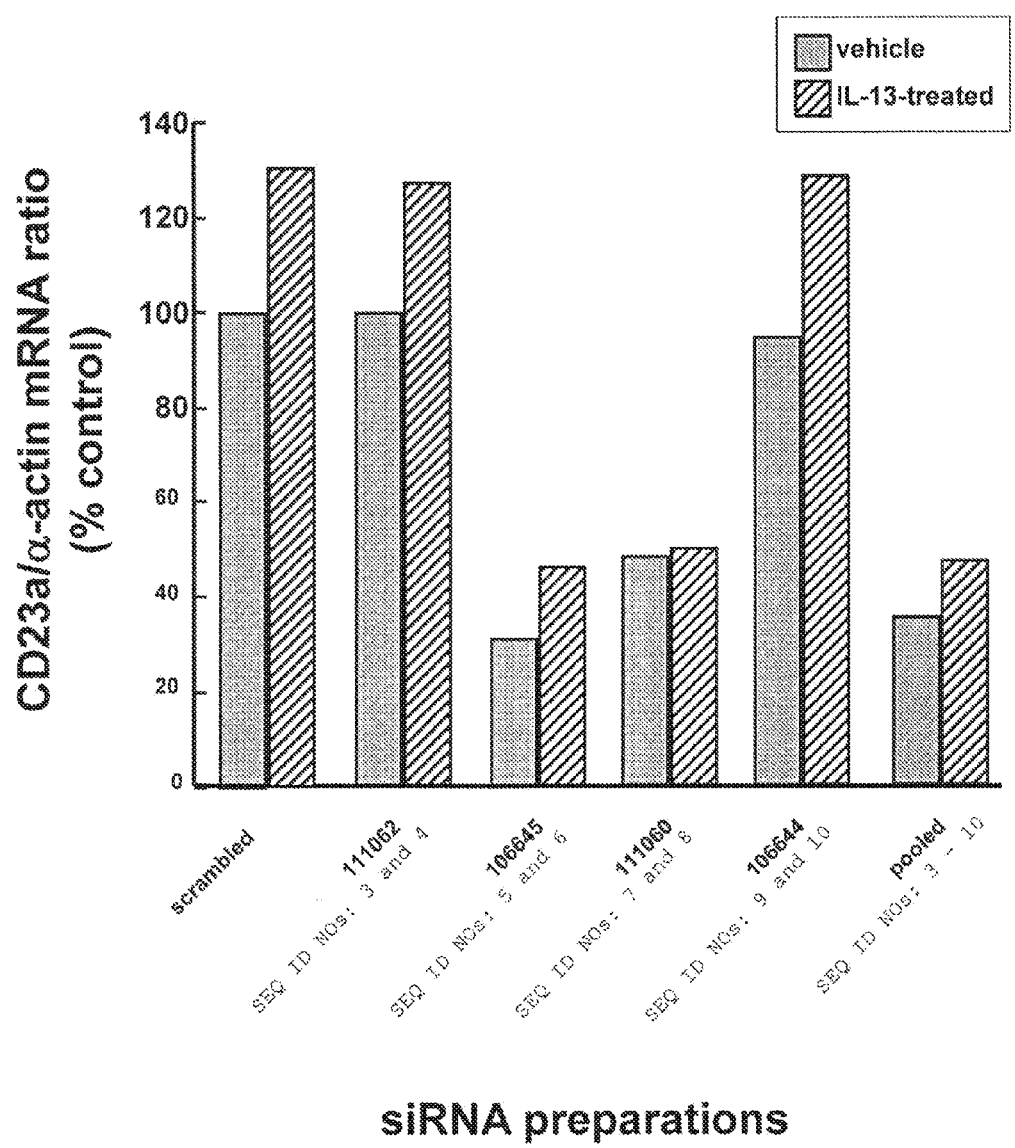

Next, the effectiveness of CD23 siRNA for inhibiting constitutive and IL-13-stimulated ASM cells was tested. Relative to vehicle-exposed ASM cells, human ASM cells constitutively express CD23a mRNA and its expression is upregulated in ASM cells pretreated with the pro-asthmatic cytokine, IL-13. The results shown in FIG. 3 demonstrate that ASM cells transfected with siRNA 106645 (SEQ ID NOs: 5 and 6) or 111060 (SEQ ID NOs: 7 and 8) show that CD23 mRNA expression is markedly inhibited in both vehicle and IL-13-treated cells. Oligofectamine-mediated transfection of human ASM cells with specific siRNA duplexes directed against CD23 markedly inhibits both constitutive expression and IL-13-induced upregulated expression of CD23.

EXAMPLE 3

Inhibition of Asthmatic-Like Changes in Constrictor and Relaxation Function in ASM Tissue Passive sensitization of isolated naïve airway smooth muscle (ASM) tissue with human atopic asthmatic serum induces changes in the tissue's agonist-mediated constrictor and relaxant responsiveness that phenotypically resemble the pro-asthmatic state (Hakonarson et al., 1995, Am. J. Physiol. Lung Cell Mol. Physiol. 269: L645-L652). To examine whether these effects of atopic asthmatic serum are mediated, at least in part, by the presence of elevated levels of IgE in the sensitizing serum, constrictor and relaxation responses were separately examined in airway segments that were treated with human control or atopic asthmatic serum in the absence and presence of CD23 siRNA. Accordingly, the effectiveness of siRNA in inhibiting the induction of asthmatic-like changes in function in isolated naïve ASM tissues passively sensitized with serum isolated from allergic asthmatic rabbits was assessed.

Figure 4:
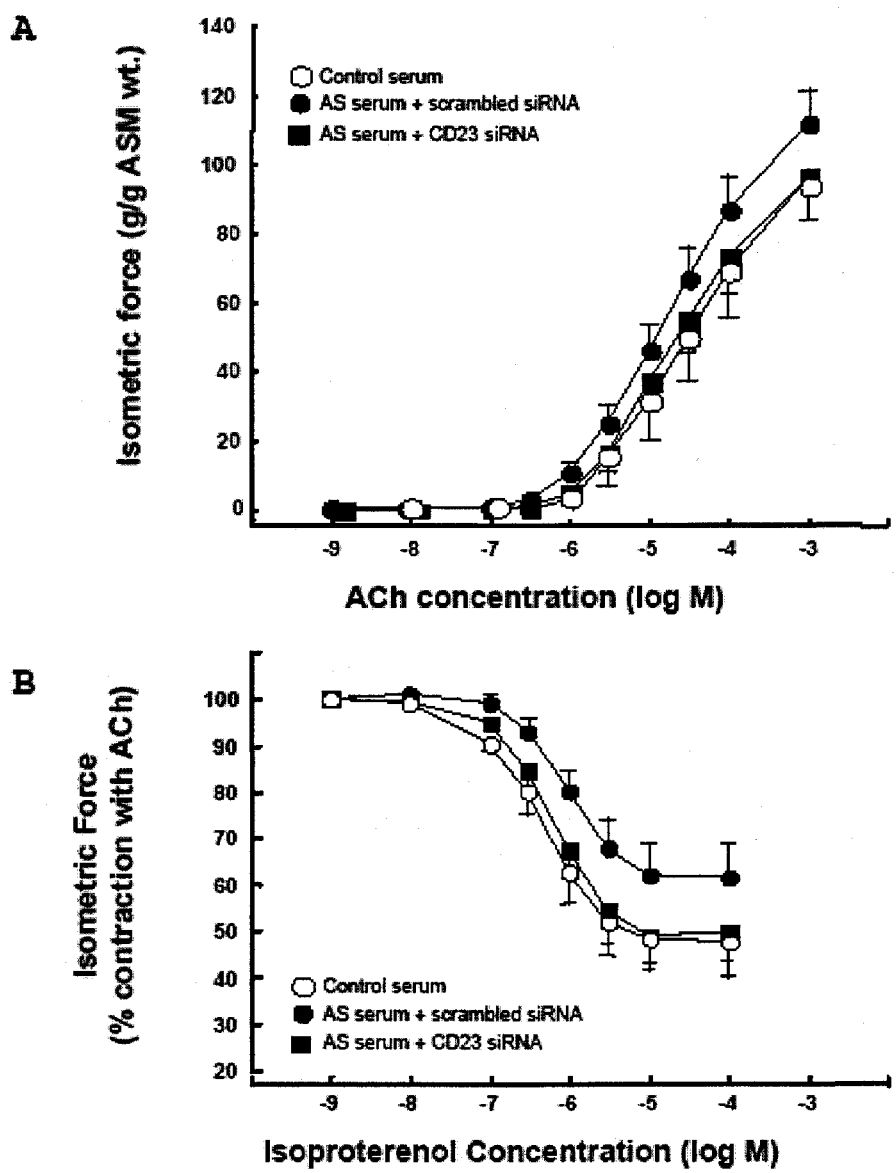

As shown in FIG. 4A, relative to tissues incubated with control serum (open circles), the maximal constrictor (Tmax) responses to ACh were significantly enhanced in passively sensitized ASM with atopic asthmatic serum and scrambled siRNA (filled circles). The induced augmented constrictor responses to ACh, however, were largely prevented in atopic serum-sensitized tissues that were pre-treated with CD23 siRNA (FIG. 4A; filled squares).

In separate studies, administration of the beta-adrenergic receptor agonist, isoproterenol, elicited cumulative dose-dependent relaxation of the pre-contracted segments as shown in FIG. 4B. The attenuated isoproterenol-induced relaxation responses were ablated in atopic serum-sensitized ASM that were pretreated with CD23 siRNA (FIG. 4B, filled squares). Both the experiments in FIGS. 4A and 4B incorporate a pool of the four siRNA duplexes used in FIGS. 2 and 3 and discussed in the materials and methods section above.

Figure 5:
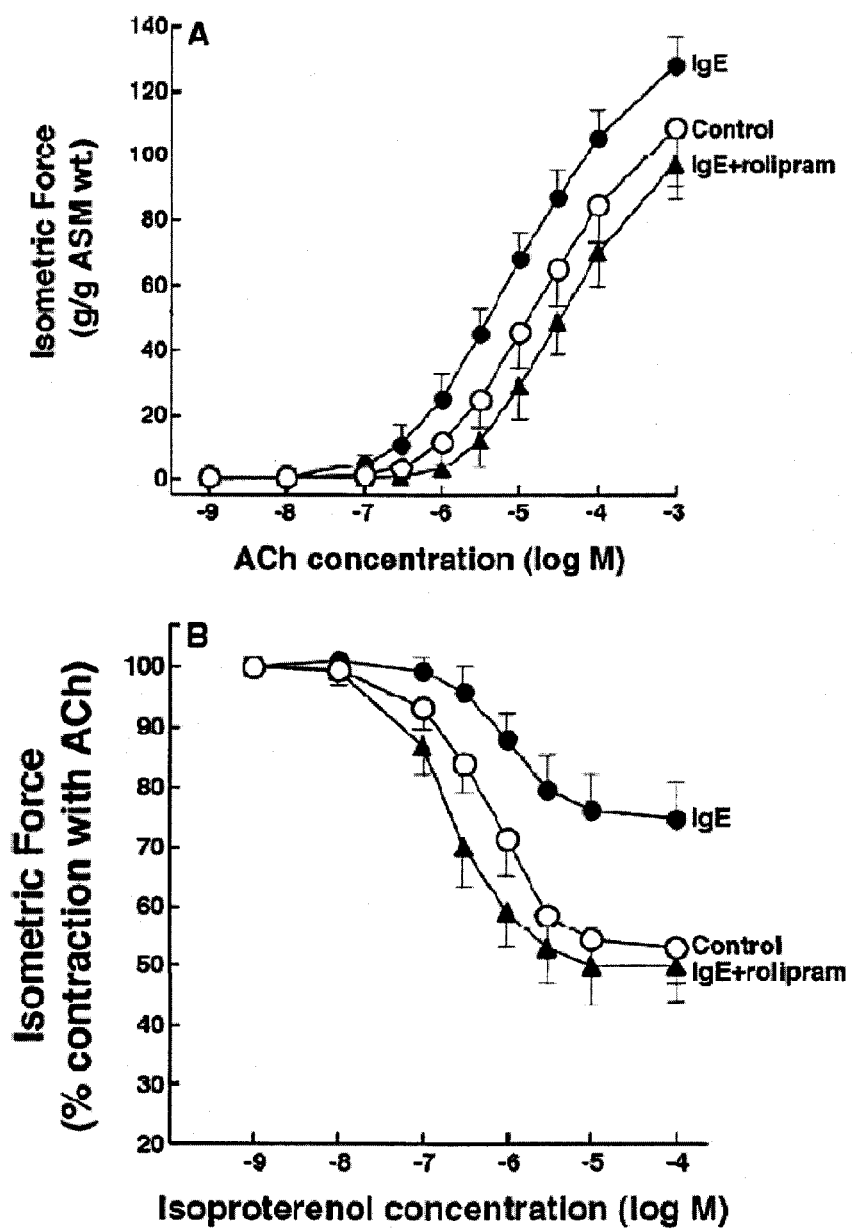

As discussed above, we have further characterized the role of CD23 in regulating the proasthmatic phenotype in ASM, and demonstrated the efficacy of using siRNA targeted against CD23 to prevent the induction of increased cAMP phosphodiesterase 4 (PDE4), which is responsible for the induction of pro-asthmatic changes in constrictor and relaxation responsiveness in asthmatic serum-sensitized and in IgE-sensitized ASM. Specifically, we have demonstrated the following:

1) ASM tissues passively sensitized with serum isolated from allergic asthmatic rabbits exhibit pro-asthmatic changes in ASM function. Specifically, the data reveal that: 1) naïve rabbit ASM tissues that are exposed for 24 hr to IgE immune complexes also exhibit pro-asthmatic changes in constrictor and relaxation responsiveness; and 2) these induced changes in constrictor and relaxation responsiveness are prevented in IgE-exposed tissues that are pretreated with the PDE4 inhibitor, rolipram (10 µM) (FIGS. 5A and 5B, respectively). Of note, these findings concur with those discussed in the previous examples which demonstrated that the pro-asthmatic changes in constrictor and relaxation responsiveness elicited in rabbit ASM tissues following their prolonged heterologous or homologous beta2-adrenergic receptor desensitization are also attributed to upregulated PDE4 activity. See Hu et al., (2008) Am J. Physiol. Lung Cell Mol Physiol. 294: L1055-L1067; Nino et al., (2009) Am J Physiol Lung Cell Mol Physiol. 297: L746-L757; and Nino et al., (2010) J Allergy Clin Immunol. 125: 1020-1027, 2010. Thus, it appears that upregulated PDE4 activity is fundamentally responsible for eliciting the pro-asthmatic phenotype in ASM tissues under different conditions of pro-asthmatic sensitization.

Figure 6:
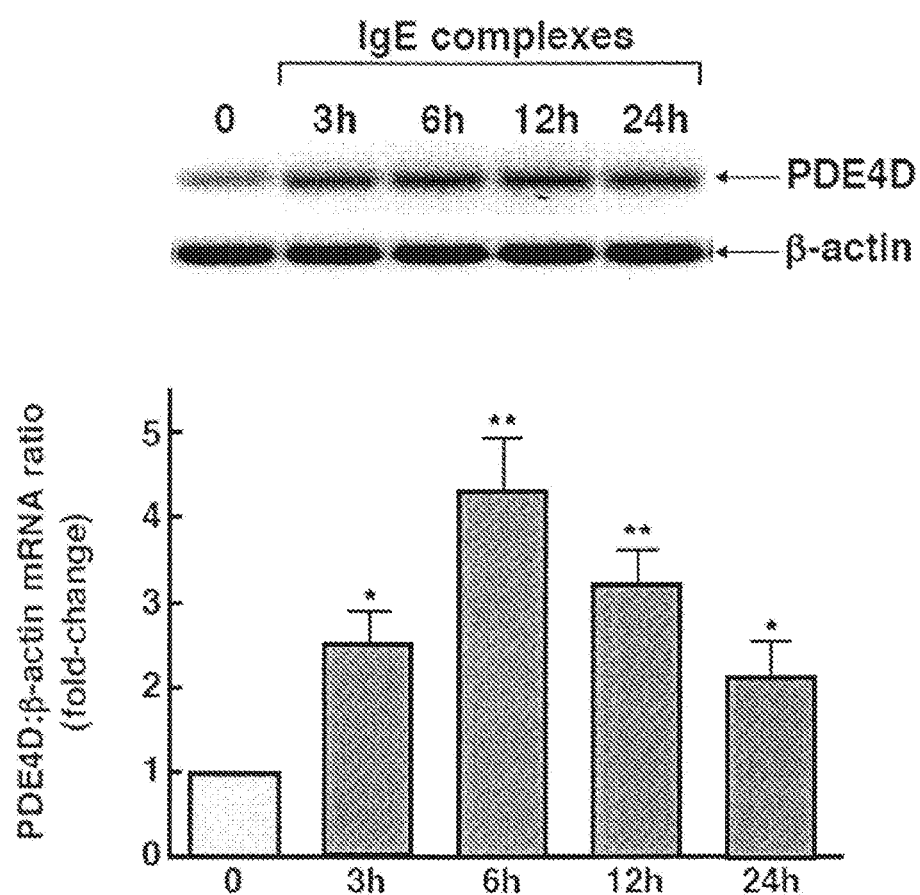

In concert with the above findings, the data in FIG. 6 demonstrate that IgE immune complexes elicit up-regulated PDE4D mRNA expression in cultured human ASM cells, with peak expression of transcripts detected at 6 hr and sustained upregulated expression of PDE4D mRNA exhibited at 24 hr following IgE administration.

Figure 7:
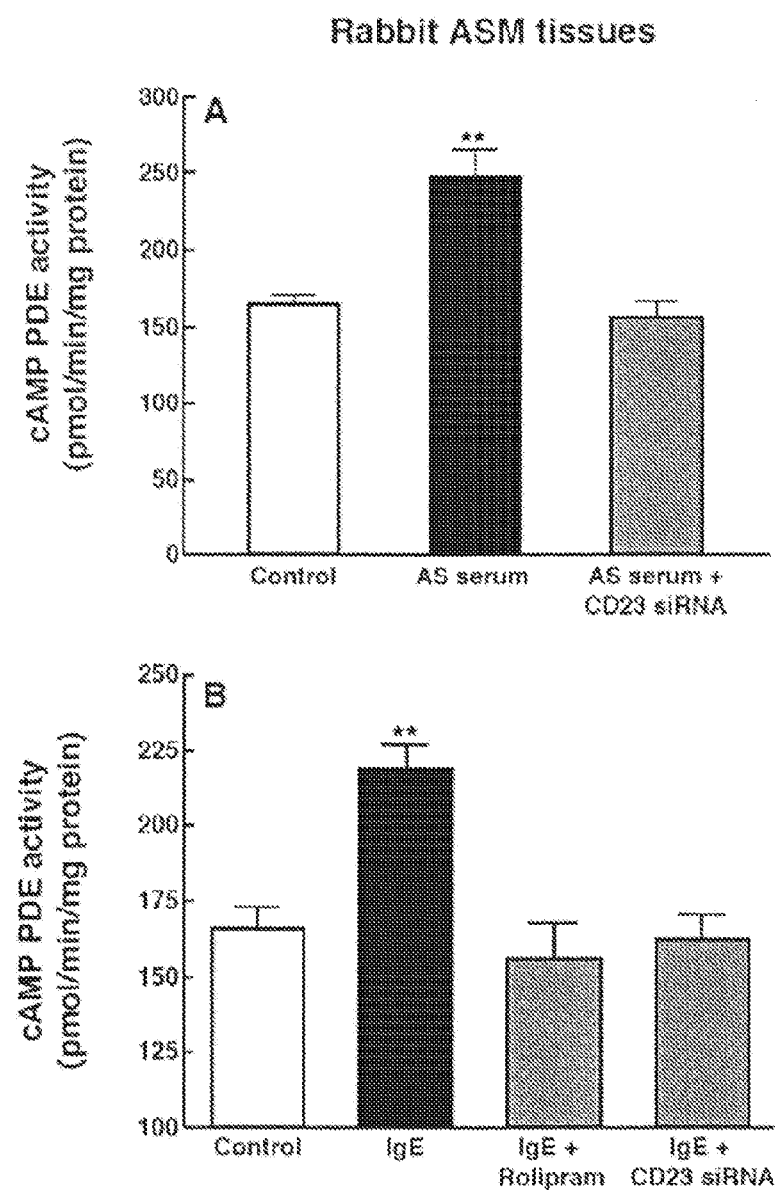

The data provided in FIG. 7 demonstrate that: 1) upregulated cAMP PDE4 activity is detected in naïve rabbit ASM tissues that are passively sensitized for 24 hr either with serum from allergic asthmatic rabbits (FIG. 7A) or with IgE immune complexes (FIG. 7B); and 2) this induced upregulation of PDE4 activity is prevented by pretreating the allergic serum- or IgE-exposed tissues with CD23 siRNA, i.e., similar to the inhibitory effect of pretreatment of IgE-exposed tissues with rolipram.

Taken together, these recent data provide evidence demonstrating that: 1) upregulated PDE4 activity is responsible for the induction of pro-asthmatic changes in constrictor and relaxation responsiveness in allergic asthmatic serum- or IgE-sensitized ASM tissues; and 2) the induction of PDE4 activity in these sensitized tissues is attributed to activation of CD23, the low affinity receptor for IgE, by the sensitizing serum or IgE complexes,; and 3) pretreatment with siRNA directed against CD23 prevents the induction of upregulated PDE4 activity under these pro-asthmatic sensitizing conditions.

The results shown here demonstrate that naïve rabbit ASM tissues that are passively sensitized with serum from allergic asthmatic rabbits exhibit increased constrictor responses to Ach and impaired relaxation responses to isoproterenol. The pro-asthmatic-like changes in ASM constrictor and relaxation responsiveness are prevented in asthmatic serum-sensitized tissues that are pre-treated with siRNAs targeted against CD23. The present findings are the first to demonstrate that airway delivery of specific siRNA duplexes targeted against CD23 represents a novel approach to treat allergic asthma.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A method of inhibiting the expression of CD23 in a patient in need thereof comprising administering to the pulmonary system of said patient an effective amount of siRNA molecules comprising a mixture of SEQ ID NO: 3-SEQ ID NO: 10 that direct cleavage of a target CD23 mRNA sequence present in said patient thereby effecting said inhibition.

2. The method of claim 1, wherein said siRNA molecules are introduced directly into said patient.

3. The method of claim 2, wherein said siRNA molecules are aerosolized for delivery.

4. The method of claim 2, wherein said patient is a human.

5. The method of claim 4, wherein said human is a patient suffering from asthma and said siRNA molecules are administered to treat said asthma.

6. The method of claim 5, further comprising the administration of at least one anti-inflammatory agent selected from the group consisting of steroidal anti-inflammatory agents and non-steroidal anti-inflammatory agents.

7. The method of claim 6, wherein said at least one steroidal anti-inflammatory agent is selected from the group consisting of dexamethasone, beclomethasone, fluticasone, triamcinolone and budesonide.

8. The method of claim 6, wherein said at least one non-steroidal anti-inflammatory agent is selected from the group consisting of IgE inhibitors, phosphodiesterase inhibitors, methylxanthines, leukotriene modifiers, anti-cholinergic agents, and beta-adrenergic agents.

9. The method of claim 6, wherein said at least one non-steroidal anti-inflammatory agent is selected from the group consisting of indomethacin, ibuprofen, naproxen, diclofenac, sulindac, oxaprozin, diflunisal, bromfenac, piroxicam, etodolac, fenoprofen, and sodium cromolyn.

* * * * *